(12) United States Patent
Rubbert et al.

(10) Patent No.: US 7,471,821 B2
(45) Date of Patent: Dec. 30, 2008

(54) METHOD AND APPARATUS FOR REGISTERING A KNOWN DIGITAL OBJECT TO SCANNED 3-D MODEL

(75) Inventors: Rüdger Rubbert, Berlin (DE); Hans Imgrund, Berlin (DE); Peer Sporbert, Berlin (DE); Stephan Maetzel, Berlin (DE); Thomas Weise, Berlin (DE)

(73) Assignee: OraMetrix, Inc., Richardson, TX (US)

(*) Notice: Subject to any disclaimer, the term of this patent is extended or adjusted under 35 U.S.C. 154(b) by 63 days.

(21) Appl. No.: 10/136,607

(22) Filed: May 1, 2002

(65) Prior Publication Data

US 2003/0021453 A1    Jan. 30, 2003

Related U.S. Application Data

(63) Continuation-in-part of application No. 09/835,039, filed on Apr. 13, 2001, now Pat. No. 6,648,640, and a continuation-in-part of application No. 09/835,007, filed on Apr. 13, 2001, now Pat. No. 7,027,642, and a continuation-in-part of application No. 09/560,645, filed on Apr. 28, 2000, now Pat. No. 6,728,423, and a continuation-in-part of application No. 09/560,644, filed on Apr. 28, 2000, now Pat. No. 6,413,084, and a continuation-in-part of application No. 09/560,583, filed on Apr. 28, 2000, now Pat. No. 6,738,508, and a continuation-in-part of application No. 09/560,133, filed on Apr. 28, 2000, now Pat. No. 6,744,932, and a continuation-in-part of application No. 09/560,131, filed on Apr. 28, 2000, now Pat. No. 6,744,914.

(51) Int. Cl.
*G06K 9/00* (2006.01)

(52) U.S. Cl. ..................... 382/154; 382/128

(58) Field of Classification Search ............ 382/154, 382/128–132, 282, 285, 294, 313, 126; 345/415, 345/653, 664, 419; 356/12; 433/3, 24, 223, 433/29; 702/159, 167; 700/163; 250/310
See application file for complete search history.

(56) References Cited

U.S. PATENT DOCUMENTS 4,185,918 A    1/1980    DeMatteo et al. ............ 356/375

(Continued)

FOREIGN PATENT DOCUMENTS

DE    3829925    3/1990

(Continued)

OTHER PUBLICATIONS

U.S. Appl. No. 09/560,131, Rubbert et al., filed Apr. 28, 2000.

(Continued)

*Primary Examiner*—Duy M Dang
(74) *Attorney, Agent, or Firm*—McDonnell Boehnnen Hulbert & Berghoff LLP

(57) ABSTRACT

Method and apparatus for registering an object of known predetermined geometry to scanned three dimensional data such that the object's location may be verified. Such a known object may comprise a less than ideal three-dimensional (3-D) digital object such as a tooth, a dental appliance (e.g., as a tooth bracket model) or other like object, including portions thereof. Knowledge of such an object's location is generally helpful in planning orthodontic treatment, particularly where the location of the object needs to be determined or confirmed or where incomplete or poor scan data is obtained. Aspects of the present invention provide methods of effectively verifying dental appliance location and displaying appliance locations using a computer and three-dimensional models of teeth.

45 Claims, 15 Drawing Sheets

U.S. PATENT DOCUMENTS

| | | | |
|---|---|---|---|
| 4,575,805 A | 3/1986 | Moermann et al. | 364/474 |
| 4,634,278 A | 1/1987 | Ross et al. | 356/376 |
| 4,663,720 A | 5/1987 | Duret et al. | 364/474 |
| 4,825,263 A | 4/1989 | Desjardins | 356/376 |
| 4,837,732 A | 6/1989 | Brandestini et al. | 364/413.28 |
| 4,867,570 A | 9/1989 | Sorimachi et al. | 356/376 |
| 5,027,281 A | 6/1991 | Rekow et al. | 364/474.24 |
| 5,257,203 A * | 10/1993 | Riley et al. | 700/163 |
| 5,278,756 A | 1/1994 | Lemchen et al. | 364/413 |
| 5,372,502 A | 12/1994 | Massen et al. | 433/215 |
| 5,431,562 A | 7/1995 | Andreiko et al. | 433/24 |
| 5,604,817 A | 2/1997 | Massen et al. | 382/120 |
| 5,615,003 A | 3/1997 | Hermary et al. | |
| 5,649,032 A * | 7/1997 | Burt et al. | 382/284 |
| 5,715,166 A | 2/1998 | Besl et al. | 364/424.24 |
| 5,724,435 A | 3/1998 | Malzbender | 382/103 |
| 5,742,294 A | 4/1998 | Watanabe et al. | 345/425 |
| 5,748,199 A | 5/1998 | Palm | 345/473 |
| 5,879,158 A * | 3/1999 | Doyle et al. | 433/24 |
| 5,937,083 A | 8/1999 | Ostuni | 382/131 |
| 5,969,357 A * | 10/1999 | Todokoro et al. | 250/310 |
| 5,970,499 A | 10/1999 | Smith et al. | 707/104 |
| 5,975,893 A | 11/1999 | Chishti et al. | 433/6 |
| 6,047,078 A | 4/2000 | Kang | 382/107 |
| 6,049,743 A | 4/2000 | Baba | 700/163 |
| 6,068,482 A | 5/2000 | Snow | 433/223 |
| 6,081,739 A | 6/2000 | Lemchen | 600/407 |
| 6,099,314 A | 8/2000 | Kopelman et al. | 433/213 |
| 6,114,695 A * | 9/2000 | Todokoro et al. | 250/310 |
| 6,167,151 A | 12/2000 | Albeck et al. | 382/154 |
| 6,217,334 B1 * | 4/2001 | Hultgren | 433/215 |
| 6,253,164 B1 | 6/2001 | Rohm et al. | 703/2 |
| 6,266,453 B1 | 7/2001 | Hibbard et al. | |
| 6,330,523 B1 * | 12/2001 | Kacyra et al. | 702/159 |
| 6,363,163 B1 | 3/2002 | Xu et al. | 382/130 |
| 6,405,071 B1 | 6/2002 | Analoui | 600/425 |
| 6,405,151 B1 | 6/2002 | Fujii et al. | |
| 6,434,265 B1 * | 8/2002 | Xiong et al. | 382/154 |
| 6,434,278 B1 | 8/2002 | Hashimoto | 382/285 |
| 6,450,807 B1 * | 9/2002 | Chishti et al. | 433/24 |
| 6,466,892 B2 | 10/2002 | Fujii et al. | |
| 6,476,803 B1 * | 11/2002 | Zhang et al. | 345/419 |
| 6,488,503 B1 | 12/2002 | Lichkus | 433/202 |
| 6,512,994 B1 | 1/2003 | Sachdeva | 702/167 |
| 6,542,249 B1 * | 4/2003 | Kofman et al. | 356/601 |
| 6,549,288 B1 | 4/2003 | Migdal et al. | |
| 6,553,138 B2 | 4/2003 | Rozin | |
| 6,616,444 B2 * | 9/2003 | Andreiko et al. | 433/3 |
| 6,621,491 B1 * | 9/2003 | Baumrind et al. | 345/419 |
| 2004/0015327 A1 * | 1/2004 | Sachdeva et al. | 702/167 |

FOREIGN PATENT DOCUMENTS

| | | |
|---|---|---|
| DE | 4218219 | 12/1993 |
| DE | 4445552 | 6/1995 |
| DE | 4436500 | 11/1995 |
| DE | 19638727 | 3/1998 |
| EP | 0250993 | 6/1987 |
| EP | 0391532 | 3/1990 |
| EP | 0294577 | 12/1998 |
| JP | H9-21620 | 1/1997 |
| JP | 2000113193 | 4/2000 |
| WO | WO0180761 | 11/2001 |

OTHER PUBLICATIONS

U.S. Appl. No. 09/560,132, Rubbert et al., filed Apr. 28, 2000.
U.S. Appl. No. 09/560,583, Rubbert et al., filed Apr. 28, 2000.
U.S. Appl. No. 09/835,007, Rubbert et al., filed Apr. 13, 2001.
S.M. Yamany and A.A. Farag, "A System for Human Jaw Modeling Using Intra-Oral Images" in *Proc. IEEE Eng. Med. Biol. Soc. (EMBS) Conf.*, vol. 20, Hong Kong, Oct. 1998, pp. 563-566.
S.M. Yamany, A.A. Farag, David Tasman, A.G. Farman, "A 3-D Reconstruction System for the Human Jaw Using a Sequence of Optical Images," *IEEE Transactions on Medical Imaging*, vol. 19, No. 5, May 2000, pp. 538-547.
Charles A. Pelizzari et al., "Accurate Three-Dimensional Registration of CT, PET, and/or MR Images of the Brain", *Journal of Computer Assisted Tom*, 13(1):20-26, Jan./Feb., 1989.
Klaus D. Toennies et al., "Registration of 3D Objects and Surfaces", IEEE, *Computer Graphics & Applications 1990*, pp. 52-62.
Behrooz Kamgar-Parsi et al., "Registration of Multiple Overlapping Range Images: Scenes without Distinctive Features", *IEEE Transactions on Pattern Analysis and Machine Intelligence*, vol. 13, No. 9, Sep. 1991, pp. 857-871.
Hui Li et al., "Registration of 3-D Multimodality Brain Images by Curve Matching", *IEEE*, 1994, pp. 1744-1748.
Jean-Francois Mangin et al., "Nonsupervised 3D Registration of PET and MRI Data Using Chamfer Matching", *IEEE*, 1993, pp. 1262-1264.
Yee et al., *"Three-Dimensional Imaging System", Optical Engineering*, vol. 33, No. 6, pp. 2070-2075 (Jun. 1994).
Related Application, U.S. Appl. No. 09/835,007, filed Apr. 13, 2001.

* cited by examiner

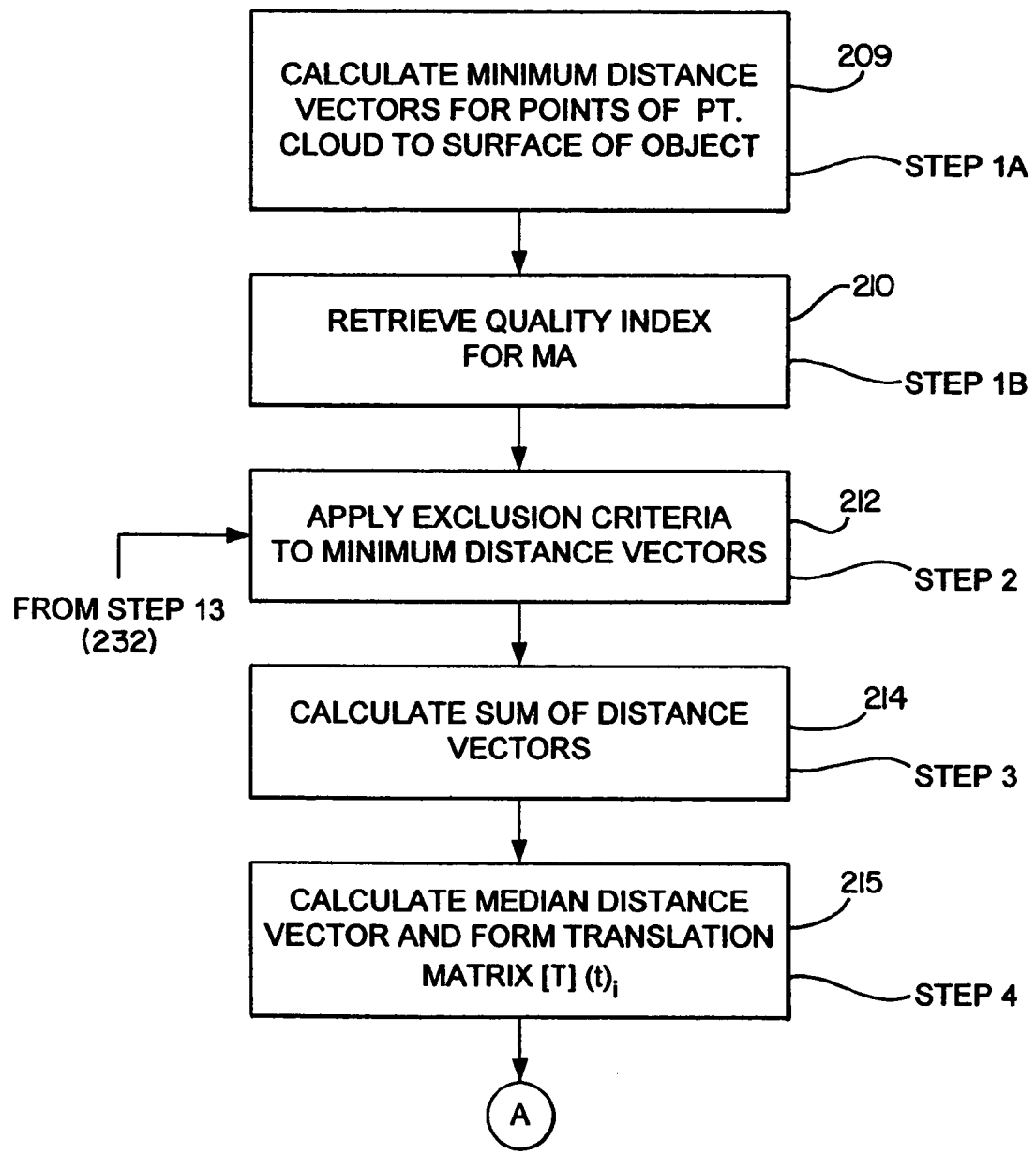

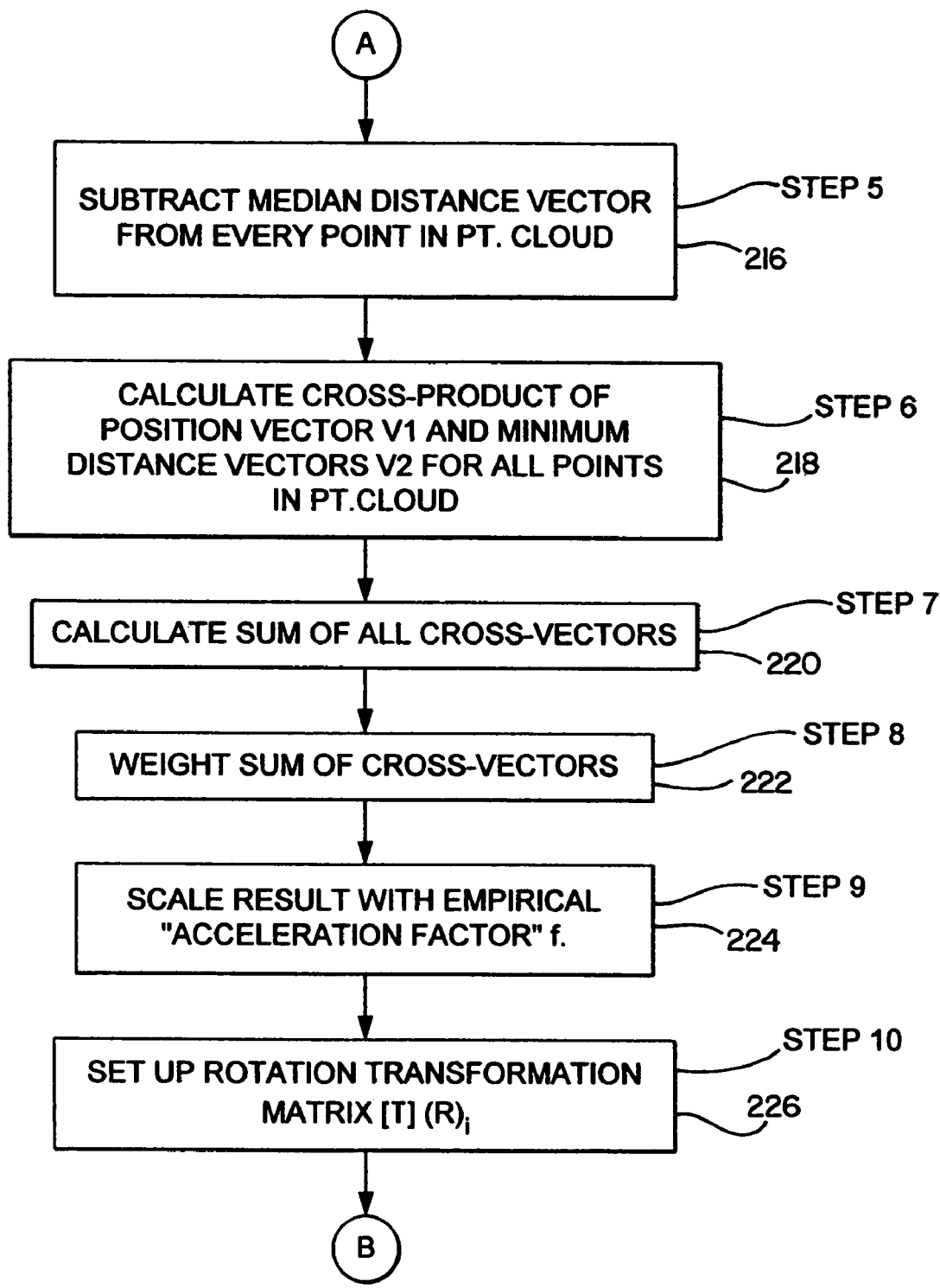

METHOD AND APPARATUS FOR REGISTERING A KNOWN DIGITAL OBJECT TO SCANNED 3-D MODEL

CROSS-REFERENCE TO RELATED APPLICATIONS

This application is a continuation-in-part application of the following U.S. Patent applications:

Ser. No. 09/835,007, filed Apr. 13, 2001, now issued as U.S. Pat. No. 7,027,642;

Ser. No. 09/835,039, filed Apr. 13, 2001, now issued as U.S. Pat. No. 6,648,640;

Ser. No, 09/560,131, filed Apr. 28, 2000, now issued as U.S. Pat. No. 6,744,914;

Ser. No. 09/560,583, filed Apr. 28, 2000, now issued as U.S. Pat No. 6,738,508;

Ser. No. 09/560,645, filed Apr. 28, 2000, now issued as U.S. Pat. No. 6,728,423;

Ser. No. 09/560,644, filed Apr. 28, 2000, now issued as U.S. Pat. No. 6,413,084;

Ser. No. 09/560,133, filed Apr. 28, 2000, now issued as U.S. Pat. No. 6,744,932.

The entire contents of each of the above patent applications is incorporated by reference herein.

BACKGROUND OF THE INVENTION

A. Field of the Invention

This invention relates generally to the fields of dentistry and orthodontics. More particularly, the invention relates to methods and apparatus for registering an object of known predetermined geometry to scanned three dimensional data such that the object's location in space may be verified. Such a known object may comprise a three-dimensional (3-D) digital object such as a virtual dental appliance (e.g., a virtual tooth bracket) or other like object. Knowledge of such an object's location is generally helpful in planning orthodontic treatment, particularly where the location of the appliance needs to be determined or confirmed or where incomplete or poor scan data is obtained. Aspects of the present invention provide methods of effectively verifying bracket location and displaying bracket locations using a computer and three-dimensional virtual models of teeth.

B. Description of Related Art

In orthodontics, a patient suffering from a malocclusion is typically treated by bonding brackets to the surface of the patient's teeth. The brackets have slots for receiving an archwire. The bracket-archwire interaction governs forces applied to the teeth and defines the desired direction of tooth movement. Typically, the bends in the wire are made manually by the orthodontist. During the course of treatment, the movement of the teeth is monitored so as to track the movement of the teeth. Corrections to bracket positions and/or wire shape can made manually by the orthodontist.

One key efficiency in treatment and maximum quality in results is a realistic simulation of the treatment process. Today's orthodontists have the possibility of taking plaster models of the upper and lower jaw, cutting the model into single tooth models and sticking these tooth models into a wax bed, and lining them up in the desired position. This approach allows for reaching a desired occlusion while minimizing guess work. A next step is bonding a bracket at every tooth model. This would tell the orthodontist the geometry of the wire to run through the bracket slots to receive a desired result.

Different types of bracket bonding methods may be implemented. In a first method, a bracket placement tray is used. In the bracket placement tray method, a placement tray is utilized to bond the various brackets to the tooth. With the bracket placement tray method, the general location of bracket placement is known. Each bracket and bracket location can be stored in memory for future retrieval.

Alternatively, a more traditional manual method may be used where the treating physician manually bonds a bracket to each tooth. In such a manual process, the actual bracket placement is not generally known and therefore cannot be stored for future retrieval during the treatment planning phase.

Hand-held scanners for in-vivo scanning of dentitions have now become available. One such scanner is described in the PCT Patent Application of OraMetrix, Inc. publication no. WO 01/80761 which is herein incorporated entirely by reference. Because a hand-held scanner allows for scans of the dentition in a relatively short time frame, the scanner can be used to perform an original scan of the patient's dentition. Based on this original scan, an original 3-D virtual model of the patient's dentition can be derived, including a virtual model of each individual tooth. This information is then digitally recorded in some fashion, preferably in a patient record stored in a memory of a scanning node in the scanner system or in an orthodontic workstation.

The scanner becomes an important tool throughout the monitoring treatment process. For example, as the treatment progresses, the movement and position of the teeth can be quantified with a relatively high degree of precision. One way to monitor the movement and position is by performing dentition monitoring scans throughout the various phases of treatment. Monitoring scans, like the original scan, provide a three dimensional virtual image of the dentition, including dental appliances, such as bonded brackets, archwires, and inlays.

Performing monitoring scans provide certain advantages. For example, one such advantage is that monitoring scans allow an orthodontist to discern whether correction in an archwire configuration may be required. For example, during the treatment process, certain biological influences may affect tooth movement. As disclosed in the above-referenced published PCT Application WO 01/80761, treatment planning software can be used to determine whether such corrections need to be made. For example, the treatment planning software on a workstation displays the current situation, and also the target situation. A new customized archwire may be designed on the computer. The relevant information for making the new archwire is sent to a precision appliance service center and a new archwire is fabricated according to revised patient requirements and then shipped to the clinic.

Monitoring scans are also useful to measure and quantify progress while detecting deviations from the expected treatment. Since each of the tooth objects of a current patient's dentition is already stored as a virtual tooth model after completion of an original scan, the monitoring scan need not be of the entire dentition. Rather, during a monitoring scan, the subsequent scanning may need only be of one surface, such as the occlusal surface, or the lingual surface, or alternatively, some combination of the two.

Performing certain monitoring scans after treatment has been initiated, however, often presents certain challenges. For example, for certain scanning technologies utilizing reflected projected patterns such as described in WO 01/80167 to be successful, the scanning requires that the surface of the scanned object allow for good reflectivity in order for the scan to adequately capture the image. There are, however, a number of complications that often arise during a monitoring scan that can often result in obtaining either incomplete or inaccurate three dimensional surface information.

For example, monitoring scans are often result in providing an orthodontist incomplete scan data of the entire dentition. Because of the incomplete nature of certain monitoring scans, the resulting incomplete scan data makes the analysis of the patient's dentition difficult.

In addition, monitoring scans often attempt to acquire accurate and complete scan results of dental devices having small or minute geometrical structures. For example, a monitoring scan often involves scanning pre-positioned bonded brackets. The size of the bracket, and the bracket component parts, also pose problems in obtaining accurate scan data.

For example, FIG. 1A illustrates a typical arrangement of a bracket structure 5 of a bracket bonded to a patient's tooth. As shown in FIG. 1A, the bracket structure 5 comprises a number of straight edge portions 4a, b, c, and d extending out into space in the x, y, and z directions. The bracket also includes an archwire slot 3 having a very narrow width. These portions contain sharp edges as well as certain well defined lines. This bracket arrangement 5 also comprises two bracket wings 1a and 1b. As can be seen from FIG. 1A, these bracket wings 1a,b have a defined length L and a defined width W equal to the length of the slot 3. Obtaining accurate scan data of these types of sharp edges and lines is often difficult since these geometrical structures cause scattering and poor image acquisition. Scattering concerns are even more prevalent where a bracket structure is even more defined, for example, where the bracket structure includes more than two bracket wings.

The size of the bracket also is a concern in obtaining accurate scan data. For example, conventional brackets are often only 3×4×3 mm in size or thereabouts. The small dimension of the bracket, and therefore the bracket component parts (wings, slot, etc.) makes obtaining accurate bracket scan data even more challenging.

These various bracket edges make it difficult to obtain accurate and complete scan information, thereby making it difficult to obtain accurate and complete scan data and therefore construct a 3-D virtual model of the dentition plus brackets. Due to the small size of bracket wings, bracket slots and their related geometries, the size of the bracket structure further causes complications due to the resolution of a projected pattern that may be used in various 3D scanning technologies. For example, where a scanner utilizes a resolution of approximately 0.25 mm, obtaining a complete and accurate scan data from a wing of a bracket will be difficult. For example, wings 1a,b of bracket 5 may only be 0.8 mm. Furthermore, obtaining complete and accurate scan data for the slot 3 will be difficult not only because of the slot width but also because of shadowing issues.

Incomplete and inaccurate scan data makes it difficult to construct an accurate three-dimensional model and thereby determine where the bonded bracket actually resides in three-dimensional space. And, since it is difficult to determine the exact position in 3-D space of the bracket, there will be further difficulty in determining the exact position of the archwire slot, and therefore the required archwire configuration. These scanning inefficiencies may be further prevalent where the dentition is scanned in-vivo, that is, where the object being scanned (dental appliance) is covered with light scattering elements such as water, saliva, or other types of moisture.

Another scanning quality issue that may arise during treatment concerns performing a monitoring scan after a patient's teeth have moved, as a result of the treatment or biological process. For example, the treatment process oftentimes begins with an orthodontist making an original dentition scan of a patient beginning the treatment process and deriving an original three dimensional virtual model of the patient's dentition. As previously described, an original scan will establish an original virtual 3-D model of each tooth without any type of dental appliance previously installed. In such a situation, the complete virtual model would contain an individual virtual tooth model for each tooth, excluding dental appliances. Therefore, the previously described scanning quality concerns relating to either incomplete or inaccurate scan data would not be present.

However, for certain patients, sometime after a first scan is completed and an original three dimensional virtual model has been derived, a bracket placement tray is fabricated. The bracket placement tray enables the brackets to be bonded to the teeth. Some time later, after the bracket tray is fabricated and only after the brackets have been bonded to the dentition, the patient will undergo a monitoring scan. One reason for the monitoring scan is to confirm accurate bracket positioning (i.e., to confirm that the bracket placement tray placed the bracket at the desired location). Because of certain inherent logistical delays, the monitoring scanning process may take place a certain amount of time after the original scan was completed. For example, in certain circumstances, bracket bonding may occur 3 to 5 weeks after the original 3-D virtual model had been obtained. But during this interim 3 to 5 week time period, the teeth may have already shifted. Therefore, the resulting subsequent monitoring scan may confirm that the original virtual 3-D model is no longer correct and must therefore be updated to reflect various new tooth positions.

Consequently, based on such scanning concerns, there is a general need for a scanning method that can accurately locate an object such as an orthodontic appliance having a predetermined geometry in three-dimensional space. This need arises in the context where both complete and incomplete scan data is present. Alternatively, there is a general need for a process that can generate an accurate virtual model of the teeth and the appliance and thereby locate manually bonded brackets. There is a further need to provide a scanning method that compensates for flawed scan data that can oftentimes arise from performing an incomplete scan, particularly where the scan involves scanning a dental appliance. There is also a general need to be able to accurately obtain a three-dimensional detention model including both teeth and a dental appliance, such as bonded brackets. Another need arises where it is generally not possible to scan an object due to restrictions in certain types of scanning technologies (e.g., scan resolutions). There is also a general need to obtain a virtual 3-D tooth model of a patient's entire dentition where the patient's dentition includes a dental appliance, such as bonded brackets.

SUMMARY OF THE INVENTION

A method and apparatus is provided for registering a virtual three dimensional model to scan data. In one arrangement, a method is provided for constructing a virtual three-dimensional model of an object. This method includes the step of scanning the object and creating a three-dimensional virtual model. The three-dimensional virtual model has a first portion corresponding to scanning of a known structure forming a part of the object. The known structure has a predetermined three-dimensional configuration. The first portion is a less than an ideal three-dimensional representation of the known structure. A three-dimensional virtual object is retrieved from a memory and corresponds to the known structure. The method includes the step of registering the three-dimensional virtual object to the first portion of the three-dimensional virtual model to form a three-dimensional surface. The virtual three-dimensional model of the object is formed and includes the three-dimensional surface.

In an alternative arrangement, a workstation is adapted to form three-dimensional virtual models of objects. The workstation includes a central processing unit and a memory storing a three-dimensional virtual model of an object. The three-dimensional virtual model has a first portion corresponding to scanning of a known structure forming a part of the object. The memory stores a three-dimensional virtual object corresponding to the known structure. The workstation includes software that is executable by the central processing unit for registering the three-dimensional virtual object to the first portion to form a three-dimensional surface and for forming a virtual three-dimensional model of the object. The virtual three-dimensional model of the object includes the three-dimensional surface.

In yet an alternative arrangement, an apparatus for constructing a virtual three-dimensional model of an object is provided. The apparatus includes a means for scanning the object and a means for creating a three-dimensional virtual model of the object from a scanning step with the aid of a computer. The three-dimensional virtual model has a first portion that corresponds to scanning of a known structure forming a part of the object. The known structure is of predetermined three-dimensional configuration. The first portion is a less than an ideal three-dimensional representation of the known structure. The apparatus includes means for retrieving a three-dimension virtual object from a memory, the three-dimensional virtual object corresponding to the known structure. Means for registering the three-dimensional virtual object to the first portion of the three-dimensional virtual model to form a three-dimensional surface is also provided. The apparatus also includes a means for forming the virtual three-dimensional model of the object, wherein the three-dimensional model includes the three-dimensional surface.

In yet an alternative arrangement, a method of constructing a virtual three-dimensional model of an object having a predefined geometry from a scanner, a data processing system, and at least one machine-readable memory accessible to the data processing system is provided. The method includes the steps of:

(a) scanning the object with the scanner in order to receive a data set related to the object;

(b) obtaining a stored digital image of the object having a known geometry; and (d) processing the data set resulting from the scan so as to register the scan data relative to the stored digital image.

In yet another arrangement, a method of determining a location of a virtual three-dimensional model of an object of known geometry is provided. This method includes the steps of:

a) scanning the known object in a series of scans, each scan generating a set of images;

b) converting the set of images into a point cloud;

c) pulling a digital representation of the virtual three-dimensional known object from memory; and d) registering the point cloud to the digital representation to thereby verify in three-dimensional space a position of the virtual three-dimensional model.

These and many other aspects and features of will be explained in more detail in the following description of a present invention implementation.

BRIEF DESCRIPTION OF THE DRAWINGS

Presently preferred embodiments of the invention are described below in conjunction with the appended drawing figures, where like reference numerals refer to like elements in the various views, and wherein:

FIGS. 11A-C provide a process for finding a best fit between the digital bracket model of FIG. 9 and the bracket scan data illustrated in FIG. 8.

DETAILED DESCRIPTION OF PREFERRED EMBODIMENT

Overview

Figure 1A:
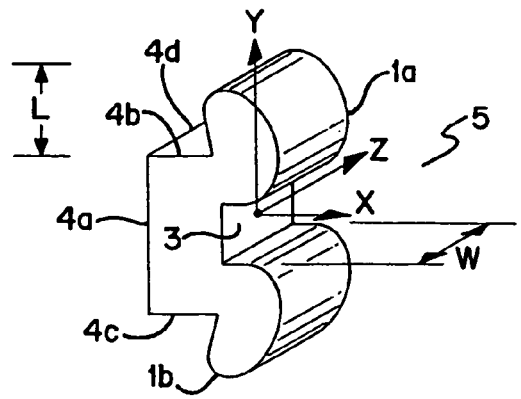
FIG. 1A is an illustration of a conventional bracket used in orthodontics.
Figure 1B:
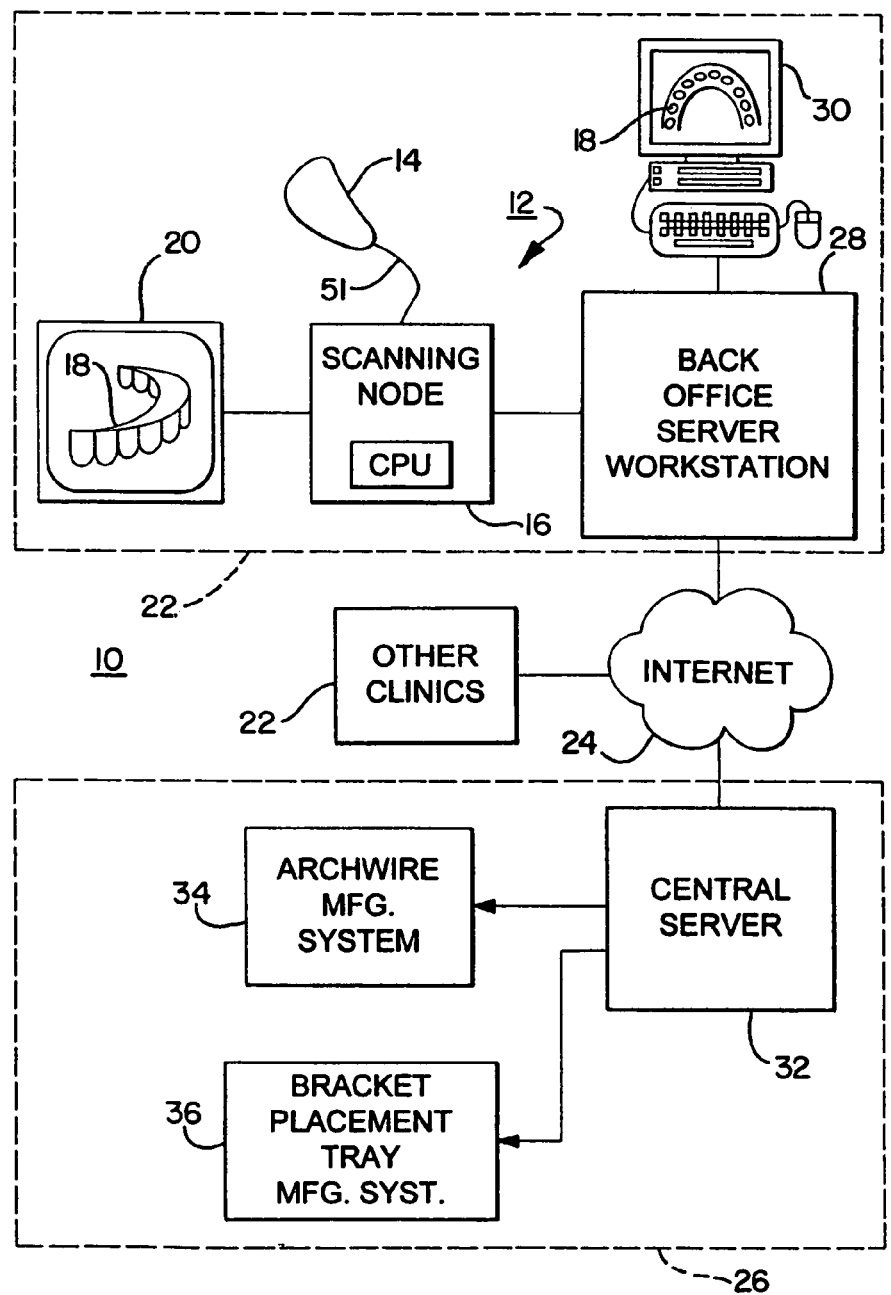
FIG. 1B is an illustration of an orthodontic care system incorporating a hand-held scanner system, suitable for performing both original and monitoring scans.

FIG. 1B is an illustration of an orthodontic care system 10 incorporating a scanner system 12. The scanner system 12 includes a hand-held scanner 14 that is used by the orthodontist or his assistant to acquire three-dimensional information of the dentition and associated anatomical structures of a patient. The images are processed in a scanning node or workstation 16 having a central processing unit, such as a general-purpose computer. The scanning node 16, either alone or in combination with a back-office server 28, generates a three-dimensional computer model 18 of the dentition and provides the orthodontist with a base of information for diagnosis, planning treatment, and monitoring care for the patient. The model 18 is displayed to the user on a monitor 20 connected to the scanning node 16.

The orthodontic care system consists of a plurality of orthodontic clinics 22 which are linked via the Internet or other suitable communications medium 24 (such as the public switched telephone network, cable network, etc.) to a precision appliance service center 26. Each clinic 22 has a back office server work station 28 having its own user a portion of a bracket interface, including a monitor 30. The back office server 28 executes an orthodontic treatment planning software program. The software obtains the three-dimensional digital data of the patient's teeth from the scanning node 16 and displays the model 18 for the orthodontist.

The treatment planning software includes features to enable the orthodontist to manipulate the model 18 to plan treatment for the patient. For example, the orthodontist can select an archform for the teeth and manipulate individual tooth positions relative to the archform to arrive at a desired or target situation for the patient. The software moves the virtual teeth in accordance with the selections of the orthodontist. The software also allows the orthodontist to selectively place virtual brackets on the tooth models and design a customized archwire for the patient given the selected bracket positions.

When the orthodontist has finished designing the orthodontic appliance for the patient, digital information regarding the patient, the malocclusion, and a desired treatment plan for the patient are sent over the communications medium to the appliance service center 26. A customized orthodontic archwire and a device for placement of the brackets on the teeth at the selected location is manufactured at the service center and shipped to the clinic 22. After the customized archwire has been applied to the patient's teeth, the software can be used to perform monitoring scans of the patient. In this manner, the effect the archwire has on the movement and rotation of the patient's teeth may be monitored. This enables the orthodontist to correct or amend treatment if necessary.

The scan data for the upper and lower arches is processed to "cut" individual tooth objects from the model. Each individual tooth model is a three-dimensional tooth object having a single set of points defining the boundaries of the tooth. The sum of these points for each image comprises a "frame." The individual tooth model reduces the amount of data required to represent the tooth, as compared to the data representing the tooth after a cumulative registration of a large number of frames. Individual tooth models are also invaluable in interactive orthodontic treatment planning since they can be independently moved relative to each other in simulation of treatment scenarios. The process of separating virtual teeth is described in further detail in published PCT application of OraMetrix, Inc. WO 01/80761 the content of which is incorporated entirely herein by reference.

Also stored as three-dimensional computer models in computer memory is a library of template dental appliances, such as brackets, archwires, retainers, inlays, etc. For example, the library of dental appliances could include the various types of brackets and other structures from various dental appliance manufactures such that the back office server workstation 28 could, based on some type of operator input data, retrieve a digital three dimensional model of a specified dental appliance. Such a digital model could be retrieved during the monitoring scanning process where patient identification data is entered into the system. Alternatively, such models could be retrieved where the user inputs a dental appliance manufacturer, a dental appliance identification number, or other identifying characteristics of the dental appliance. In yet another alternative scenario, these models may be retrieved automatically by a registration algorithm, as discussed in detail below.

As with the virtual three-dimensional tooth model, the various individual dental appliance models in the library of three-dimensional models are three-dimensional models having a single set of points defining the boundaries of the object.

Individual appliance models are also invaluable in interactive orthodontic treatment planning since they can be independently manipulated relative to each other in simulation of treatment scenarios. As further discussed in detail below, the individual appliance models also facilitate 3-D registration of objects of known geometry such as teeth models and other models of various types of dental appliances including brackets, archwires, removable aligning devices, retainers, Herbst appliances, etc. to scan data.

As shown in FIG. 1B, the precision appliance service center 26 includes a central server 32, an archwire manufacturing system 34 and a bracket placement manufacturing system 36. These details are not particularly important to the scanning system 12 per se and are therefore omitted from the present discussion for sake of brevity. For more details on these aspects of a representative orthodontic care system, the interested reader is directed to the above cited published PCT application and the patent application of Rüdger Rubbert et al., entitled "Interactive and Archwire-Based Orthodontic Care System Based On Intra-Oral Scanning of Teeth," Ser. No. 09/835,039 filed Apr. 13, 2001, the contents of which are incorporated by reference herein.

Figure 2:
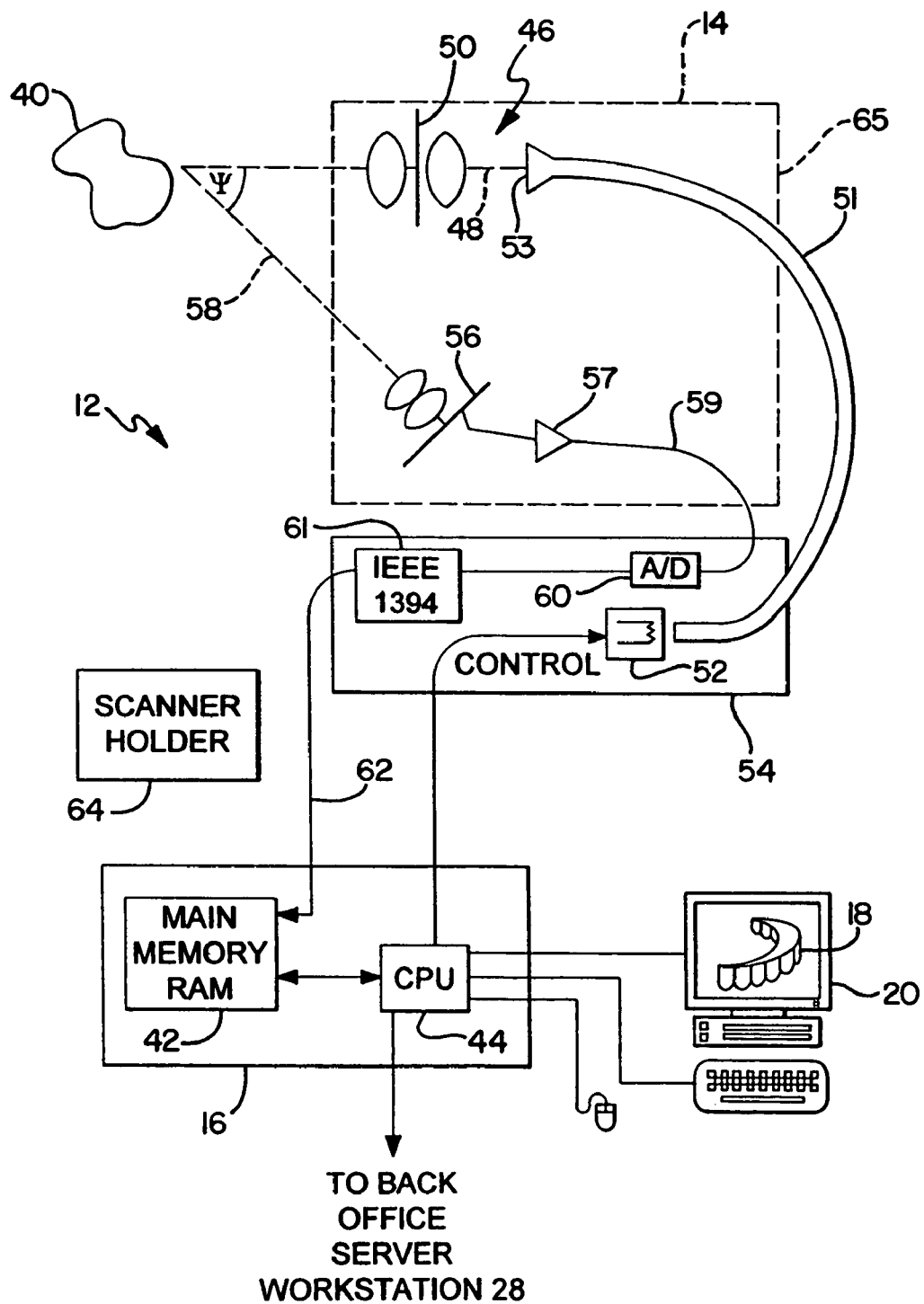
FIG. 2 is a block-diagram of a scanning system, suitable for use in the orthodontic care system of FIG. 1B.

FIG. 2 is a more detailed block-diagram of the scanning system 12, suitable for use in the orthodontic care system of FIG. 1B. The scanning system 12 is a mechanism for capturing three-dimensional information of an object 40, which in the present example is the dentition and surrounding anatomical structures of a human patient, e.g., gums, bone and/or soft tissue. The captured 3-D image may include a dental appliance. The scanning system 12 includes a scanner 14 which is used for image capture, and a processing system, which in the illustrated example consists of the main memory 42 and central processing unit 44 of the scanning node or workstation 16.

The scanner 14 includes a projection system 46 that projects a pattern onto the object 40 along a first projection axis 48. The projected pattern is formed on a slide 50 which is placed in front of a light source 53. In the illustrated embodiment, the light source 53 comprises the terminus of a fiber-optic cable 51. The cable 51 carries a high intensity flash generated by a flash lamp 52 located in a base unit 54 for the scanner. A suitable flash lamp is the model FX-1160 flash unit available from Perkin Elmer. The illuminations of the flash lamp 52 cause the pattern contained in the slide 50 to be projected onto the three-dimensional surface of the object. Further details on the types of patterns suitable for the pattern are set forth in the following co-pending patent applications of Rüdger Rubbert et al., Ser. No. 09/254,755 filed Mar. 9, 1999; Ser. No. 09/560,131 filed Apr. 28, 2000, and Ser. No. 09/673,863 filed Nov. 30, 2000 assigned to the assignee of the present invention, the contents of which are entirely incorporated by reference herein.

The electronic imaging device 56 forms an image of the projection pattern after reflection of the pattern off of the surface of the object 40. The reflected patterns imaged by the imaging device contain three-dimensional information as to the surface of the object, and this information needs to be extracted from the images. Each image captured by the imaging device 56 is converted to a 3-D point cloud, referred to herein as a "frame." The scanning system therefore includes a processing subsystem which is used to extract this information and construct a three-dimensional virtual model of the object 40. In the preferred embodiment, this processing subsystem consists of a memory 42 storing calibration information for the scanner, and at least one processing unit, such as the central processing unit 44 of the scanning workstation 16. The location of the memory and the processing unit is not important. They can be incorporated into the scanner 14 per se. Alternatively, all processing of the images can take place in the back office server 28 or in another computer. Alternatively, two or more processing units could share the processing in order to reduce the amount of time required to generate the three-dimensional information.

The memory 42 stores a calibration relationship for the scanner 14. The calibration relationship, which can be in the form of a table or one more mathematical functions, comprises information used to compute three-dimensional coordinates of points on the object that reflected the projection pattern onto the imaging device. The information is obtained during a calibration step, performed at the time of manufacture of the scanner 14. The calibration information includes an array of data storage locations that contain two pieces of information. Firstly, a calibration table stores pixel coordinates in X and Y directions for numerous portions of the projection pattern that are imaged by the electronic imaging device 56, when the pattern is projected onto a calibration surface at two different distances during a calibration procedure. Secondly, the table stores distance information, (e.g., in units of tenths of millimeters), in X and Y directions, for the portions of the projection pattern imaged at the two different distances. For more details on these aspects of the presently preferred scanner, calibration, and illustrated orthodontic care system, the interested reader is directed to the patent application of Rüdger Rubbert et al., entitled "Methods for Registration of Three-Dimensional Frames to Create Three-Dimensional Virtual Models Of Objects," Ser. No. 09/835,009 filed Apr. 13, 2001, the entire contents of which are incorporated by reference herein. The present invention can be practiced with other types of conventional scanners, such as laser scanner systems, which are known in the art.

The scanning system requires at least one processing unit to perform image processing, three-dimensional calculations for each image, and registration of frames to each other. The processing unit also performs various registration processes during monitoring scans, including dental appliance registration and, when required, tooth registration. The processing unit 44 in the illustrated embodiment is the central processing unit (CPU) of the scanning work station 16. The CPU 44 processes the image of the pattern after reflection of the pattern off the surface of the object 40 and compares data from the image to the entries in a calibration table. From that comparison, the processing unit 44 derives spatial information, in three dimensional space, of points on the object that reflect the projected pattern onto the electronic imaging device. The sum of these points for each image comprises a "frame."

Basically, during operation of the scanner, to scan an object surface configuration, hundreds or thousands of images are generated of the projection pattern as reflected off of the object in rapid succession as the scanner and object are moved relative to each other. The scanner may be used to scan an unknown object (such as scanning a dentition of a first time patient). Alternatively, the scanner may also be used to scan an object of known geometry (such as a previously scanned tooth, bonded bracket or other type of dental appliance). By known geometry, it is generally meant that a digital three dimensional representation of the object is stored in memory, preferably in the memory located at the scanning node or workstation in the system illustrated in FIG. 1B. As the handheld scanner is moved relative to the object, a series of images are recorded of the projection pattern as reflected off the object in rapid succession, each image converted to a frame. The frames are then registered to each other to create the 3-D virtual model of the object.

For each image, pixel locations for specific portions, i.e., points, of the reflected pattern are compared to entries in a calibration table. X, Y and Z coordinates (i.e., three dimensional coordinates) are obtained for each of these specific portions of the reflected pattern. For each image, the sum total of all of these X, Y and Z coordinates for specific points in the reflected pattern comprise a three-dimensional "frame" or virtual model of the object. When hundreds or thousands of images of the object are obtained from different perspectives, as the scanner is moved relative to the object, the system generates hundreds or thousands of these frames. These frames are then registered to each other to thereby generate a complete and highly accurate three-dimensional model of the object 40.

FIG. 2 also shows a few other features of the presently preferred scanning system 12. After the CCD imaging device 56 captures a single image, the analog voltage signals from the device 56 are amplified in an amplifier 57 and fed along a conductor 59 to an analog to digital converter 60. The digital signal is converted into a bitmap stream of digital image data. The data is formatted by a module 61 into an IEEE 1394 "firewire" format for transmission over a second conductor 62 to the main memory 42 of the scanner work station 16. The scanning system includes an optical scanner holder 64 for the user to place the scanner after the scanning of the dentition is complete.

The scanning work station 16 also includes the monitor 20 for displaying the scanning results as a three-dimensional model 18 of the dentition in real time as the scanning is occurring. The user interface also includes a keyboard and mouse for manipulating the virtual model of the object, and for entering or changing parameters for the scanning, identifying sections or segments of scans that have been obtained, performing dental appliance and tooth registration, as well as other features. The unit may also include a foot switch, not shown, for sending a signal to the CPU 44 indicating that scanning is commencing and scanning has been completed. The base station may alternatively include a voice recognition module that is trained to recognize a small set of voice commands such as START, STOP, AGAIN, REPEAT, SEG- MENT, ONE, TWO, THREE, FOUR, etc., thereby eliminating the need for the foot switch. Scanner start and stop commands from the CPU 44, in the form of control signals, are sent to the light source 52, thereby controlling the illumination of the lamp 52 during scanning.

Figure 3:
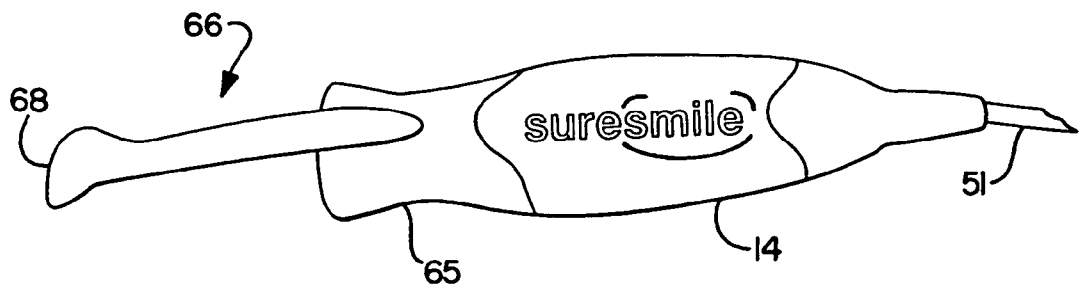
FIG. 3 is a perspective view of a hand-held scanner used to acquire information of an object (of known or unknown geometry), suitable for use in the orthodontic care system of FIG. 1B.

FIG. 3 is a perspective view of a hand-held scanner 14 used to acquire information of an object under scrutiny, suitable for use in the orthodontic care system of FIG. 1B. The projection system 46 and the electronic imaging device 56 of FIG. 2 are contained in the housing 65 for the scanner. The housing 65 is sized and shaped to be held in a human hand. The scanner 14 includes an elongate distal portion 66 having a tip 68. The tip 68 has a mirror sized and shaped such that it can be inserted into and moved within an oral cavity of a human so as to enable scanning of anatomical structures inside the oral cavity.

Figure 4:
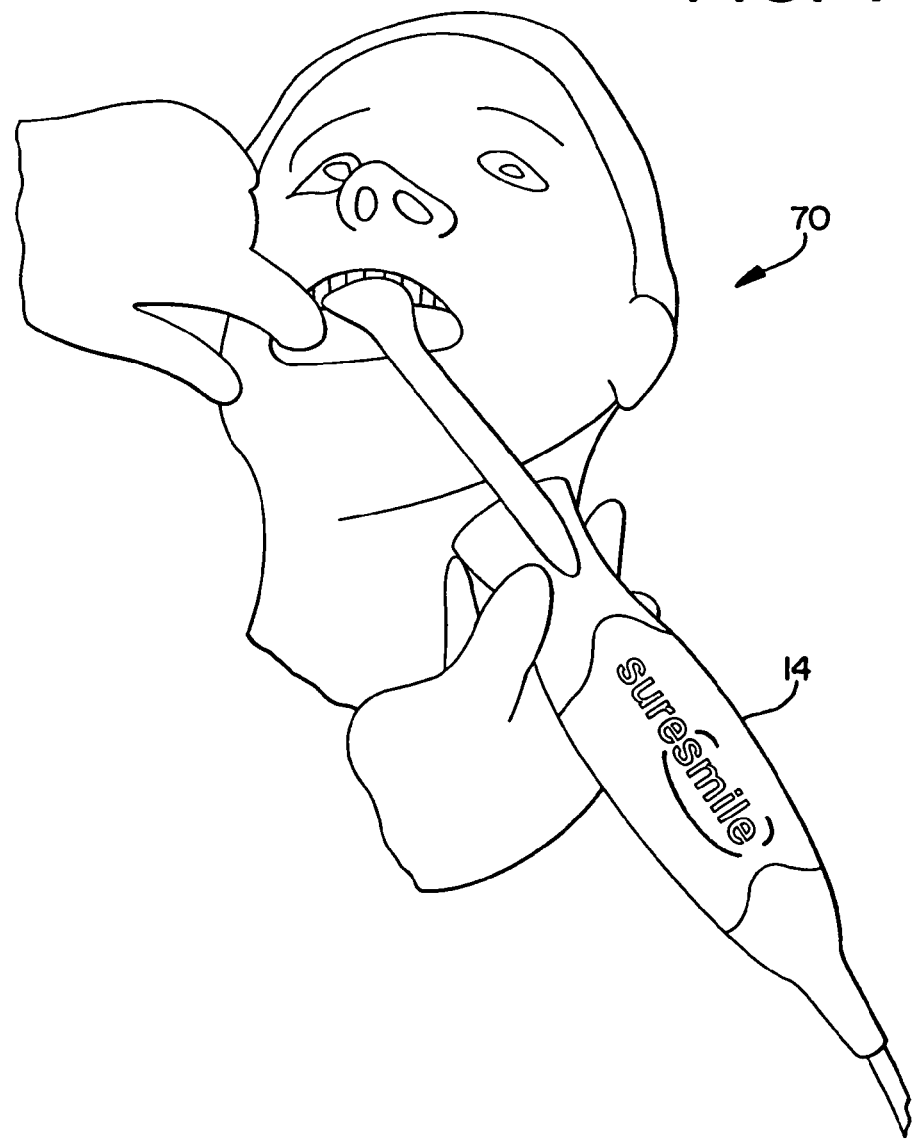
FIG. 4 is an illustration of an operator performing a scan (either an original or monitoring scan) of a patient with the hand-held scanner of FIG. 3.

FIG. 4 is an illustration of a patient 70 being scanned with the hand-held scanner 14 of FIG. 3. The patient 70 may or may not have dental appliances and may be undergoing an original or a monitoring scan. The cheeks and lips are retracted from the teeth and the tip 68 of the scanner is moved over all the surfaces of the patient's teeth, brackets, archwires, and other dental appliances in a sweeping motion at a velocity of perhaps 1-2 centimeters per second. The entire upper or lower jaw may need to be scanned in a series of scans, one for the left side, one for the right side, and one for the front. These individual scans are registered to each other. In addition, where the patient's 70 dentition includes devices of known geometry such as brackets and/or other type of dental appliance, the individual scans comprising scan data will enable the treatment software to register the derived scan data to a stored digital model of the dental appliance.

Voice commands or activation of a foot switch (not shown) indicates when each scanning segment is initiated and terminated. The entire process takes just a few minutes. Depending on the color and translucency of the object and the illumination intensity and frequency of the light source in the scanner, it may be necessary to apply a very thin coating of a reflective substance such as Titanium Dioxide to the object. Preferably, where the patient's dentition includes a dental appliance (such as brackets), a very thin coating of a certain composition of matter, such as Titanium Dioxide mixed with a binder and volatile alcohol base, is applied over these surfaces. For more details on these aspects of this composition of matter, the interested reader is directed to the patent application of Nancy Butcher et al., entitled "Method of "Wet Field" Scanning," Ser. No. 10/099,042 filed Mar. 14, 2002, the entire contents of which are incorporated by reference herein.

Figure 5:
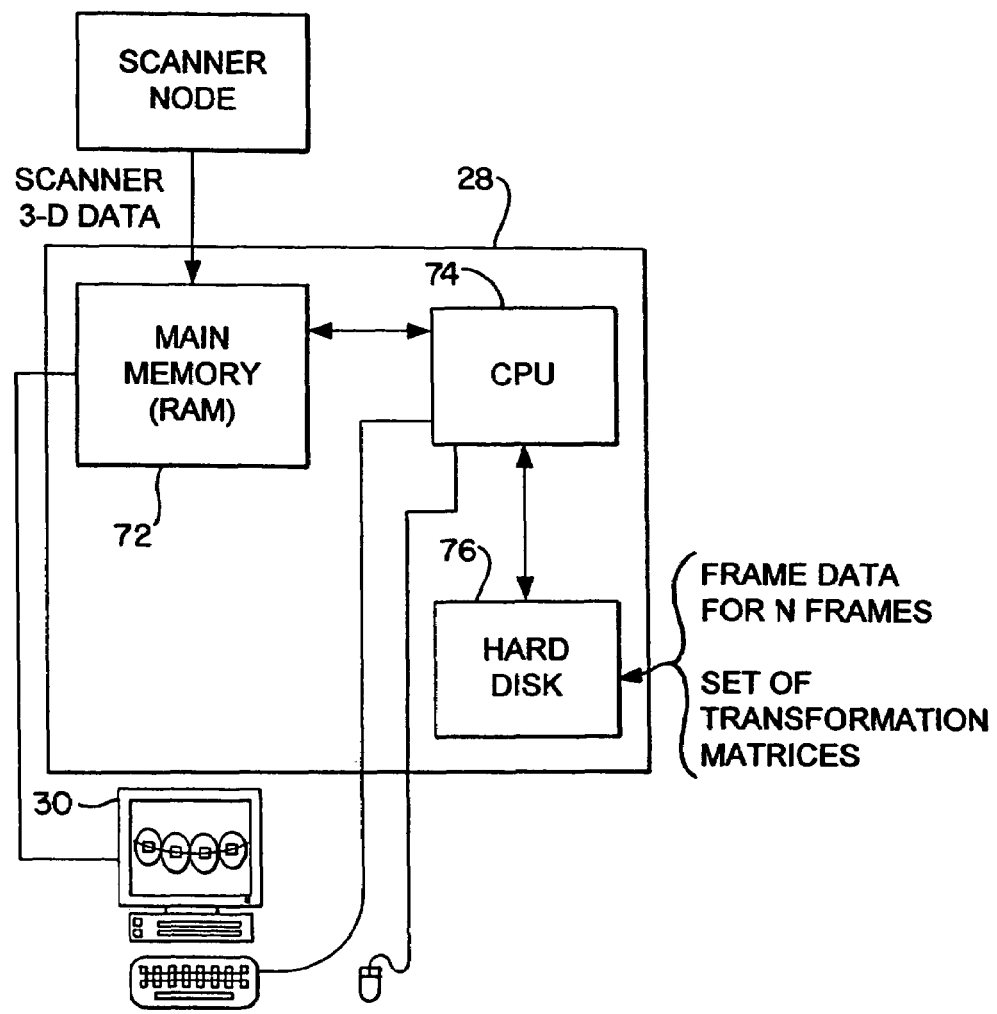
FIG. 5 is a block diagram of the back office server of FIG. 1B showing the elements used to calculate the digital model of the patient's dentition and display the digital model on a screen display of the server.

FIG. 5 is a block diagram of the back office server of FIG. 1B showing the elements used to calculate the digital model of the patient's dentition. After the scanning workstation has processed all the images captured by the scanner and generated a set of three dimensional frames, the frame data is transmitted to the back office server 28. The back office server 28 performs a cumulative registration process for the frames and ultimately generates and displays the digital model on a screen display 30. The back office server 28 can also perform a dental appliance registration process for any dental appliance within the digital model. In the event that a dental appliance registration process is performed, the back office server 28 could also initiate a tooth registration process.

The raw scanner data in the form of three-dimensional frames is stored in the main computer memory 72. The frame data for N captured images, i=1 . . . N from the scanner is stored in the hard disk 76. The hard disk also stores a set of (N−1) transformation matrices $[T]_i$, for i=2−N. The transformation matrices basically contain information as how each frame of three-dimensional points needs to be translated and rotated in a three-axis Cartesian coordinate system in order to be registered with the other frames in a best-fit manner. The transformation matrices also contain information as to how each frame of three-dimensional points needs to be translated and rotated in order to be registered with known three dimensional objects, such as dental appliances and/or virtual tooth models.

Ii is generally known that in order to arrange several three-dimensional objects with respect to one another, there are essentially two options. The first option relates to referencing all of the data to a common co-ordinate system. For example, if one component of an object would be located 1000 mm higher (i. e. in Z direction) than another component, the Z-coordinates of that first component would show values that are in general 1000 mm greater than the Z-coordinates of the other component. While this approach is easy to understand and straightforward, it has a disadvantage of being very inflexible.

In utilizing the above mentioned transformation matrices, applicants are using a different option to handling independent virtual three-D objects that are positioned in 3-D space. For example, where an object is composed of several components, such an object will be defined in such a way that each component of an object has its own (local) coordinate system. The data points belonging to such a component are then referenced to the local coordinate system. Only one additional information is then needed. This additional information relates to the location of that local coordinate system (reflecting a component of the object) within the (global) coordinate system of the object.

In this manner, an object may be composed solely from various components, so no data point would be referenced directly to the global coordinate system. Only the locations of the local co-ordinate systems would be referenced to the global system. Therefore, an efficient method of referencing a local coordinate system to a global system is a vector defining the translatory offset, and a 3×3 matrix defining the rotational offset. The vector and the matrix can also be combined to a 4×4 matrix, where the first three rows contain the values of the rotational matrix, and the last row contains the vector. Only the left three columns of the matrix would be utilized in that case. Such a 4×4 transformation matrix holds the rotational offsets as well as the translatory offset and is therefore convenient to handle. In other embodiments, the forth column of the transformation matrix could be used to define the zoom factor of the component, thus enabling not only to modify the location and orientation of the component, but also its size. This aspect, however, is not taken into consideration within this application. One advantage of applicant's concept is that a component of an object can be efficiently re-located by simply changing the values in the 4×4 matrix. The values of the component itself, since they are referring to the local co-ordinate system, remain untouched.

As will be discussed in greater detail below, a preferred arrangement of applicant's bracket registration follows this concept. In this preferred arrangement, we are dealing with objects or components of objects that have their own local coordinate system. Therefore, they can be arranged to any desired composition by assigning a transformation matrix to those objects or components.

In a broader sense, applicants are looking at objects or components or portions of objects, assuming that those components and portions have their own independent definition, and can be arbitrarily located and oriented, no matter if this is achieved by using local coordinate systems and/or transformation matrices or an other applicable mathematical approach.

Returning now to FIG. 1B, importantly, the hard disk 76 stores a library of three-dimensional virtual models. For example, such a library could include a composite set of digital models representing bracket three-dimensional models. The library may also include a library of patient records, each patient record including information relating to the three-dimensional tooth models and appliance models of existing patients.

Upon completion of the scan and upon generation of a virtual model of the patient's dentition, the above information from the treatment planning software is recorded in a patient record and sent over a suitable communications medium 24 in digital form to a precision appliance service center 26. (see FIG. 1A). The service center manufactures a customized archwire and a bracket placement tray for placement of the brackets at the intended location on the teeth in the malocclusion.

Basically, the position of the bracket slots, and the shape of the brackets, when the teeth are in a target situation, is information that is ultimately developed and stored by the treatment planning software. This position of the bracket slots and the shape of the slot (e.g., the length) is known in three dimensions. A digital image of each bracket used to fabricate a patient's bracket tray is recorded in the patient record and also stored for later retrieval. A patient data record is maintained to include the bracket tray information, including a digital representation of a three-dimensional model of each bracket bonded to the patient's teeth. Other relevant information on relevant bracket data may also be stored including a manufacturer's own bracket number, as well as other important bracket identification information. Where the brackets are bonded manually (rather than by way of a bracket placement tray), patient data record may not contain this information.

The bracket placement tray is separately manufactured using stereolighography or other similar technique. The treatment planning software superimposes the brackets on the teeth to generate a three-dimensional model comprising the three-dimensional tooth objects plus the virtual brackets at their intended locations in the observed stage or malocclusion.

This three-dimensional model is supplied to a stereolithography (SLA) instrument. The SLA instrument manufacturers a plastic model of the teeth with the model and a thermoplastic foil placed within a pressure chamber. The chamber is pressurized so that the foil envelops the dentition and the brackets. After cooling, the foil is removed from the model. The foil, now in the shape of a transfer tray, has small indentations where the brackets are located. Real brackets are placed in these indentations. The orthodontist uses indirect bonding techniques to bond the brackets to the teeth. The transfer tray positions the brackets on the teeth at the desired location. After the bonding is complete, the orthodontist removes the transfer tray, resulting in the brackets bonded to the teeth at presumably the desired location. The treatment planning software stores the precise bracket data used for each patient and can, upon an operator interface or at the initiation of the treatment planning software, access and retrieve a virtual three dimensional model representative of each of the brackets used to fabricate the transfer tray.

One important aspect of the treatment planning software records the type of bracket bonded to each particular tooth. For example, for each bracket used in the bracket bonding tray, the type and make of each bracket will be stored in the patient record by the treatment planning software. In this manner, during the various phases of treatment planning, the orthodontist or other treatment initiator will be able to retrieve the specific parameters of each bracket previously bonded to a patient's teeth. As will be discussed in greater detail, such a library of bracket information (including virtual tooth models) provides other advantages during the registration process.

Once the actual brackets have been bonded to the teeth, an orthodontist will proceed with the treatment process by initiating monitoring scans of the dentition to obtain bracket position and tooth movement information. Any unwanted deviation in the bracket position can be accounted for by modification of the archwire. Alternatively, the bracket may have to be removed and re-bonded. In the case where an individual is a first time patient but already has an archwire or other dental appliance, an original scan will be required so that an original 3-D virtual model of the dentition may be obtained so that tooth movement can be monitored. In one arrangement of the present invention, the monitoring scan data is used to register bracket scan data to a 3-D model of the bracket.

Figure 6:
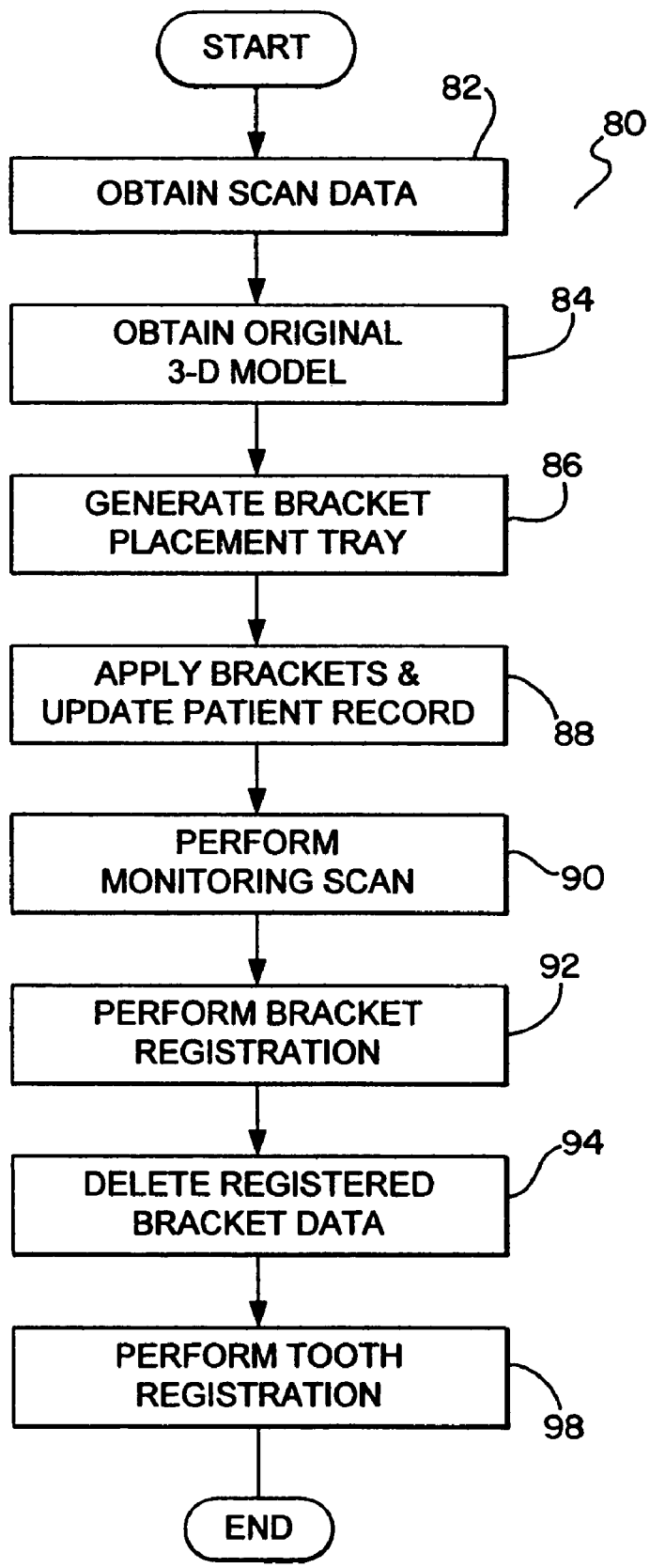
FIG. 6 is a flow diagram illustrating a method which includes, in part, a sequence of steps used by the processing unit in the scanning station to calculate three-dimensional information of an object (of known or unknown geometry) from images captured by the scanner illustrated in FIG. 3.

FIG. 6 is a flow diagram illustrating a method which includes, in part, a sequence of steps used by the processing unit in the scanning station to calculate three-dimensional information of an object (of known or unknown geometry) from images captured by the scanner illustrated in FIG. 3. First, at step 82, a patient is scanned and the scan data is obtained. This scan data comprises data for the teeth and, where a patient has a dental appliance, scan data from the appliance. Next, at step 84, the scan data is processed so that a three dimensional virtual model of the dentition is obtained. During this step, a patient record may be created and/or updated. Next, at step 86, where the patient requires bracket bonding, the brackets may be bonded manually or with a bracket tray. If a bracket tray is required a tray is generated and at step 88, the brackets are applied to the patient's teeth. The patient data record is updated to include relevant bracket data, including the specific type and geometry of each bonded bracket. Where the brackets are bonded manually, no patient data record may exist.

Next, the treatment facilitator initiates the treatment process, including performing various monitoring scans.

Generally, after a monitoring scan is performed, a registration process is used such that new scanned data relative to the existing virtual tooth model may be registered to the original virtual model derived during the original scan. By way of subsequent monitoring scans, the registration process may derive a current or an updated three-dimensional virtual model of the dentition at the point in time of treatment. For more details on these aspects of generating such a three-dimensional virtual model, the interested reader is directed to the commonly assigned patent application of Rubbert et al. entitled "Methods for Registration of Three-Dimensional Frames to Create Three-Dimensional Virtual Models of Objects," Ser. No. 09/835,007 and filed Apr. 13, 2001, the entire contents of which are incorporated by reference herein.

Study of this virtual model and comparison to the target virtual model of the teeth and the virtual model at the beginning of treatment can indicate whether the contemplated treatment is progressing as anticipated. Alternatively, such a comparison can indicate if additional correction to the orthodontic appliance needs to be made. Certain required corrections will typically be carried out as wire changes in an archwire orthodontic treatment regime, in which new bends are placed in the orthodontic archwire.

However, after the original three dimensional image has been derived and the brackets bonded to the patient's teeth, future treatment requires rescanning of the dentition. The results of subsequent dentition rescans may be compared to the original digital template of the expected bracket position. If a bracket is placed incorrectly, the bracket may need to be removed and re-bonded to the tooth. Alternatively, corrections to the archwire may be made to account for displacement of the brackets from their expected position. Basically, this is accomplished by simulating the position of the teeth with the actual bracket placement at the target situation and correcting the shape of the archwire as necessary. Alternatively, a new archwire based on the actual placement of the brackets may be obtained.

At step 90, a monitoring scan is performed wherein a scan is made of the patient's dentition, including any dental appliances. In the scenario where the system does not have an existing three-dimensional virtual image of the patient's dentition, the monitoring scan provides information that will be used to comprise an "original" scan of the patient as well. Certain scan data derived from this monitoring scan will also be used to register a stored digital model to a subset of the resulting scan data.

Then, at step 92 a bracket registration process is initiated in order to replace poor scan data from the bracket with more complete 3-D surface data from a stored 3-D model of this bracket. This process is performed for each tooth. As will be discussed in greater detail below, a first step in the bracket registration process is the positioning of a virtual bracket marker (VBM) on a subject bracket data. A digital representation of the bracket is retrieved from a digital library and the treatment software finds a best fit between the bracket scan data and this known digital virtual model of the bracket. In this manner, the precise 3-D location of a bracket bonded to the tooth can be identified and confirmed. Where the bracket was manually bonded and no patient data record information exists, the precise bracket location of each bracket can be determined. Step 92 is described in more detail below. The result of step 92 is a 3-D surface that represents the bracket bonded to the tooth in a much more complete and accurate manner, compared to the scan data.

Once the bracket registration is complete, the scanned bracket data is then extracted from the virtual model at step 94. This extraction process generates a void in the three dimensional model. A second registration process 98 is performed so that the tooth void is filled or "smoothed" with tooth data. In this manner, the tooth scan data from the monitoring scan is registered to a virtual tooth model obtained during step 84. Where no previous 3-D model exists for the patient (new patient, corrupted data, etc.) the system at step 98 pulls a template virtual tooth model from a digital library and performs a best fit algorithm so as to register the known virtual tooth model to the tooth scan data derived from step 90.

Figure 7:
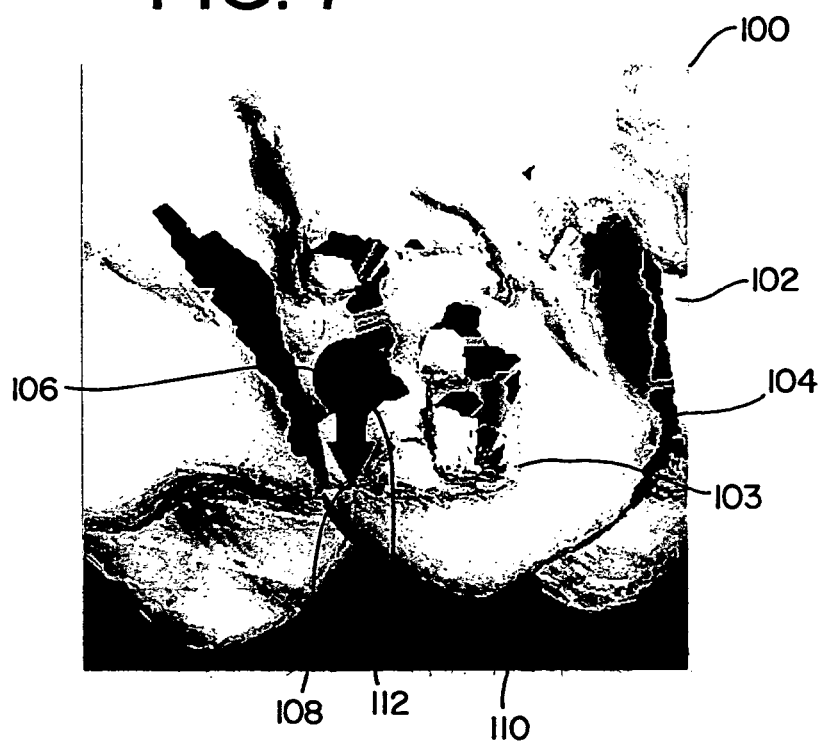
FIG. 7 is an illustration of a two-dimensional bitmap image of a tooth and associated anatomical structures captured by the electronic imaging device of the scanner illustrated in FIGS. 1, 2, 3 and 4 with a virtual bracket marker (VBM) assigned to a virtual tooth.

After a monitoring scan is completed, a 3-D model of the patient's dentition is obtained. For example, FIG. 7 provides a screen shot of a three dimension model 100 of a portion of a patient's complete 3-D dentition model. The three dimension model 100 includes scan data 102 that comprises both tooth scan data 104 and bracket scan data 103.

Methods for performing a frame to frame registration to create the model 100 shown in FIG. 7 is disclosed in related application "Methods for Registration of Three-Dimensional frames to Create three-Dimensional virtual Models of Objects," Ser. No. 09/835,007 incorporated by reference and to which the reader is directed to for further details.

FIG. 7 shows a set of a scan data derived from a monitoring scan, such as a monitoring scan performed on the patient of FIG. 4. The scan data 102, comprised of a point cloud, includes both tooth scan 104 data as well as bracket scan data 103. The complete scan data 102 could be the result of an original scan (new patient) or the result of a monitoring scan (existing patient).

Bracket data 103 provides a virtual representation of a structure of the actual bracket bonded to the tooth that is virtually represented by the tooth data 104. Such a bonded bracket could have a configuration similar to the bracket 5 illustrated in FIG. 1A. However, because of the difficulties associated with obtaining complete and accurate bracket scan data as previously discussed in detail above, the bracket scan data 103 can be a poor representation of the actual bracket bonded to tooth. For example, both the wings and hooks of the virtual bracket 103 are difficult to recognize and therefore make it difficult to actually know the position of the actual bracket on the actual tooth.

As will be discussed in detail below, a method of retrieving a stored digital bracket model from a digital library and registering this digital model against this poor bracket scan data allows for precisely identifying the actual location of the bracket on the tooth. In one embodiment, the digital stored model is retrieved from the back office server workstation 28 or at central server 32 illustrated in FIG. 1B and the bracket registration process begins at step 92.

A user initiates the bracket registration process by identifying a subject bracket scan data for registration. This can occur by applying a landmark, in this case a virtual bracket marker (VBM) 106, to the bracket data as a preliminary step in initiating registering the bracket positioned over a tooth. Alternatively, the bracket registration process may be initiated by automatically detecting a portion of the scan that may be fragmented or isolated. For example, there may be a certain recognizable scan data patterns that the registration algorithm can be programmed to identify or recognize as indicating that these patterns should be automatically interpreted as bracket scan data.

As illustrated in FIG. 7, the VBM 106 is manually positioned at a VBM point location 112 on the user interface of the workstation or scanning mode. The VBM point location 112 provides an indication to the bracket registration engine as to where in 3-D space to position, at least approximately, a virtual digital model of the bracket. Therefore, it is preferred that the VBM is placed as close to the actual bracket location as possible. However, complete accuracy in locating the VBM on the bracket scan data is not necessary for accurate bracket registration.

The VBM also comprises a VBM orientation element 108. This VBM orientation element 108 is represented in FIG. 7 by an arrow. In one possible arrangement, to place the VBM 106 on the bracket scan data 102, the user clicks on a tooth number provided in a menu of the treatment software. Tooth numbers are provided along a row of numbers provided on a user interface. The user can then drag a cursor with a hand held device (mouse) to the surface on the virtual tooth data where they wish to place the VBM 106. The user then releases the cursor, and the VBM appears on the tooth. Under most circumstances, the user will try to place the bracket marker in the center of the scan bracket data.

The VBM orientation element 108 may be manipulated so that the arrow points in the direction of an incisal edge 110 of the virtual tooth data 104. Using various control icons, the user can manipulate the VBM to place the arrow in the proper orientation by simply clicking on the VBM and turning the mouse one way or the other.

After the VBM has been positioned on the subject bracket data, the registration engine determines a best fit between the bracket scan data and previously stored bracket model pulled from a digital library of bracket models. Generally, the algorithm then looks at each point of the bracket scan data that is within a certain distance within the digital 3-D bracket model, and determines how to translate and rotate the virtual bracket model as to find a best fit between the bracket model and the scan data.

Once the VBM has been placed in an initial registration position (FIG. 7), a scan data subset is extracted from the 3-D virtual model of the patient's dentition. This scan data subset will represent only a relevant portion of the patient's dentition, thereby excluding unnecessary scan data. In one arrangement, such an extracted area comprises a volume of scan data of only the data for one entire tooth. An extracted volume of scan data can be 10 mm wide, 10 mm high, and 10 mm wide.

Figure 8:
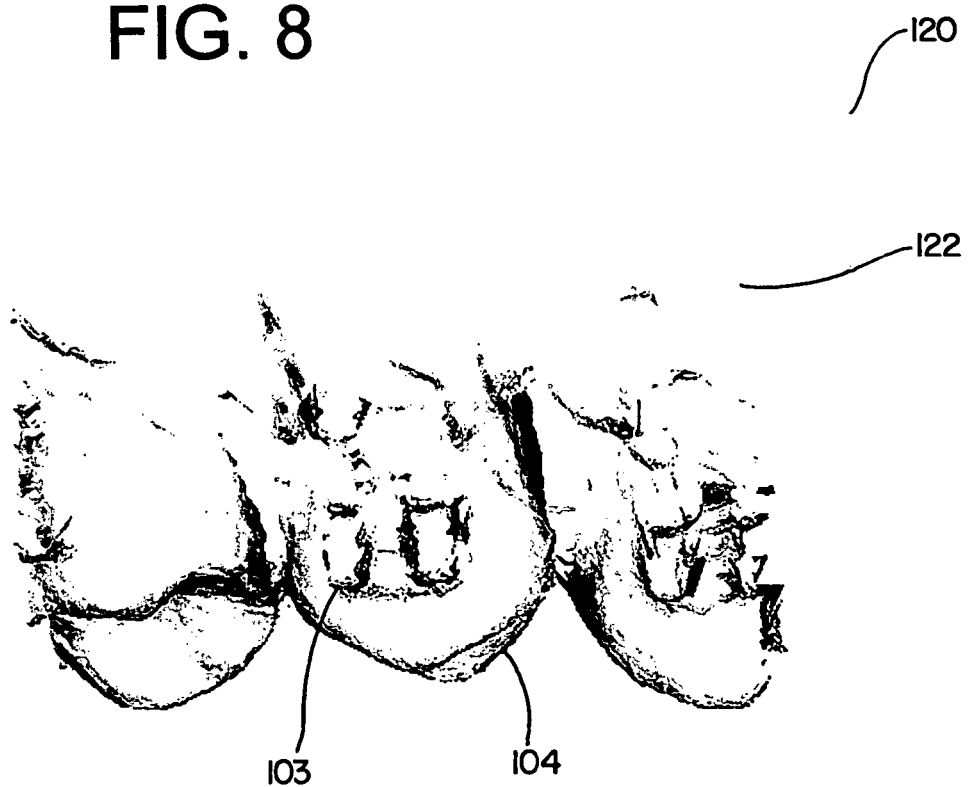
FIG. 8 provides a screen shot representing a sub-set of scan data of the 2-D bit map image identified by the bracket marker illustrated in FIG. 7.

FIG. 8 illustrates a screen shot 120 that includes a sub-set of data 122 extracted from the three dimension virtual model 100 illustrated in FIG. 7. Based on this sub-set of extracted data 120, the registration process begins the best fit process. The extracted sub-set of data 122 comprises the entire data set of points that will be processed by the bracket registration process. As illustrated in FIG. 8, the VBM is no longer provided on the scan data.

Figure 9:
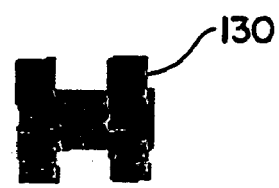
FIG. 9 provides a digital bracket image extracted from a virtual bracket library for use in the orthodontic system of FIG. 1B.

Based on information provided by the operator, the registration algorithm extracts a stored 3-D digital model of a bracket from a digital library. For example, the operator may input certain patient information so that data from the patient record may be extracted from storage. Alternatively, known bracket data information is automatically retrieved by the treatment planning software from the digital library. For example, FIG. 9 illustrates such a digital bracket model 130 that may be retrieved from a library of digital bracket models. Similarly, where the registration algorithm is used to register other types of dental appliances, such as retainers, Herbst appliances, or expansion devices, a stored digital model of the retainer or other device would be retrieved from a library of digital models.

Now, based on this retrieved bracket model 130 and the VBM point location identified by the VBM point locator 112, the registration algorithm places the retrieved digital model 130 on the tooth.

Figure 10:
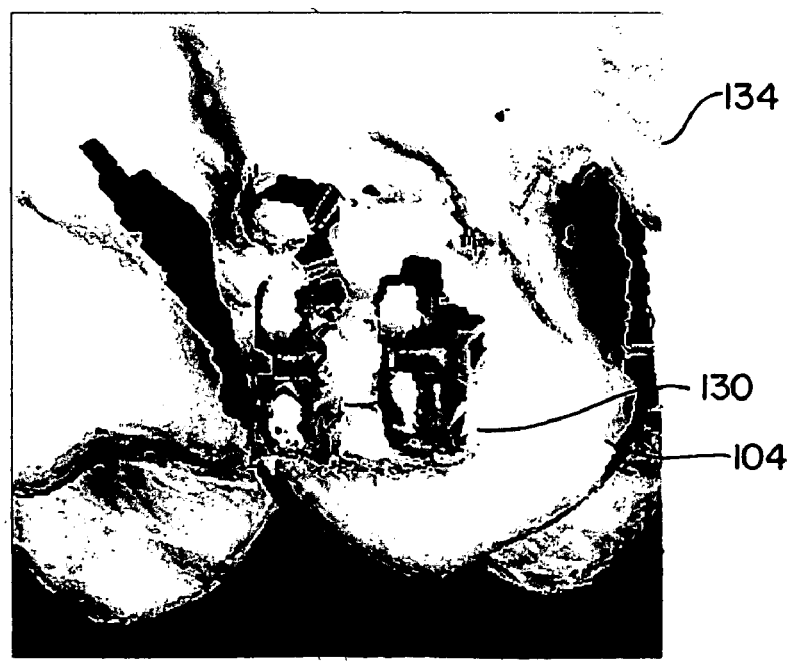
FIG. 10 illustrates the extracted virtual bracket of FIG. 9 positioned on a tooth based on the location of the bracket marker illustrated in FIG. 7.

FIG. 10 illustrates the extracted bracket model 130 illustrated in FIG. 9 residing on the sub-set tooth structure illustrated in FIG. 8. Because this virtual bracket model will not be placed exactly where the actual bracket resides in three-dimensional space, the bracket model 130 must be registered to the bracket scan data illustrated in FIG. 8 to find a best fit between the model 130 and the scan data.

Figure 12A:
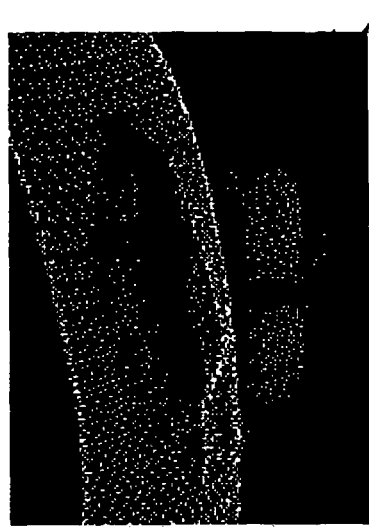
FIG. 12A illustrates a point cloud of scan data.
Figure 12B:
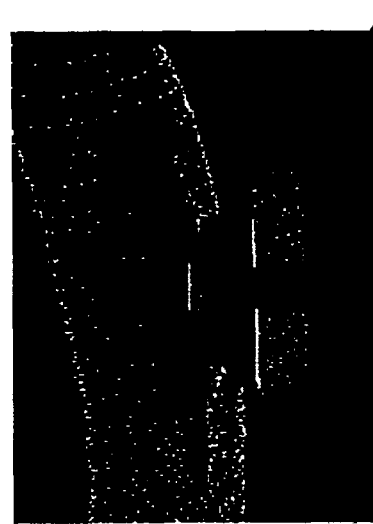
FIG. 12B illustrates a digital bracket model registered to the point cloud of scan data illustrated in FIG. 12A.

Point cloud to object registration is a preferred process for registering the scan data to the digital model of the bracket. For example, FIG. 12A illustrates a point cloud 140 comprising both tooth scan data 142 and bracket scan data 144. The point cloud to object registration process will then find a best-fit in terms of translation and rotation of the virtual bracket model to make points in the point cloud agree with a digital model, such as the digital bracket model illustrated in FIG. 9. For example, FIG. 12B illustrates the result of the bracket registration process wherein the digital bracket model has been registered to the bracket data scan of FIG. 12A.

Figure 11C:
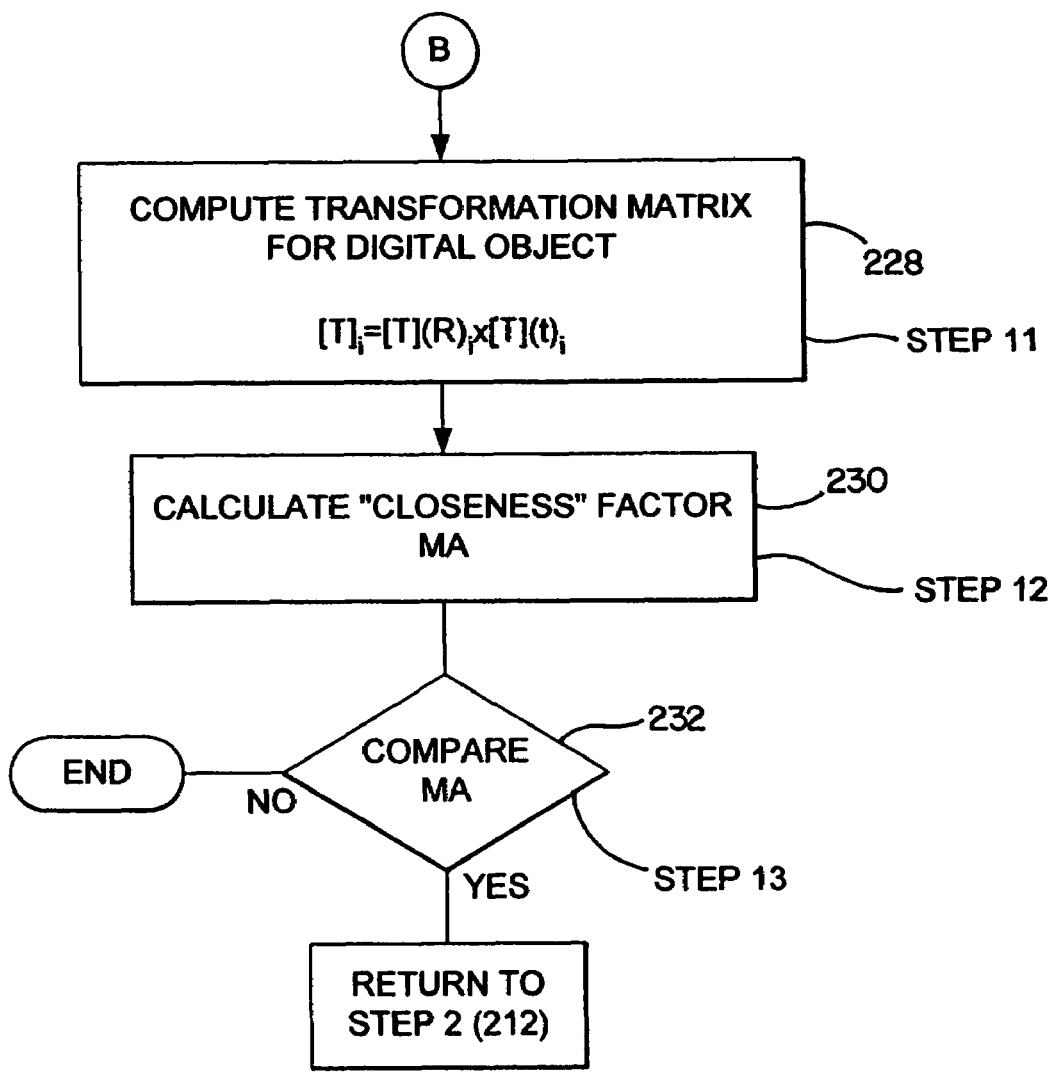

FIGS. 11A-11C is a flow chart of a point cloud to object registration process for point cloud and an object of known three-dimensional shape. Here, the object is a known digital object (such as a virtual tooth, tooth template, bracket, dental appliance, tooth, etc.). The registration process is used to find a best fit between the point cloud relative to the known object, and thereby provide a more accurate three-dimensional model for the scanned object.

The end result of the frame to model registration is a substantially exact three dimensional model of the scanned object positioned in three-dimensional space. This model is represented by a large set of point coordinates in computer memory. The result can also be represented as a set of transformation matrices providing information as to how individual frames forming the point cloud should be translated and rotated in three dimensions in order to fit to the known model. Alternatively, the result may be represented as a set of a set of transformation matrices providing information as to how the object should be translated and rotated in three dimensions in order to fit to the point cloud.

Referring now to FIGS. 11A-C, the registration procedure begins with step 1A, 209 in FIG. 11A. At step 1A, minimum distance vectors 248 (N1, N2, . . . ) are calculated from every point in the point cloud representing the scan data to the surface of the digital object. The surface of an object can be obtained by connecting neighborhood points together with a triangle or other polygon. The minimum distance vector, for each point in the point cloud, is defined as the distance vector having a magnitude which is the minimum of the following three vectors: 1) the shortest vector from the point intersecting a triangle surface of the object normal to the triangle surface; 2) the shortest vector from the point orthogonal to the edge of a triangle surface of the object, and 3) the shortest vector from the point to the nearest point of the object. Most often, but not always, this will be a normal vector, type 1) above.

At step 1 (210 in FIG. 11A) an initial quality index for the closeness factor MA is retrieved. The relevance of quality index to the closeness factor will be described with respect to step 12 (232) of FIG. 12B.

At step 2 (212), three exclusion criteria are applied to the minimum distance vectors of step 1, in order to eliminate non-overlapping data points between the point cloud and the object and to eliminate stray data points. First, all minimum distance vectors that relate to a boundary element (edge or point) in the point cloud are excluded. Second, remaining minimum distance vectors with an amount exceeding a certain predefined value R, likely indicating stray data points, are excluded. Thirdly, only triangle surfaces are taken into consideration which form the outside surface with respect to the scanner viewing direction. Each surface has by definition two sides. The "outside" surface is regarded as the surface of the object that is oriented towards the scanner.

At step 3 (214) the vector sum of all the minimum distance vectors $N_1 \ldots N_N$ is computed.

At step 4 (215), the median minimal distance vector (t) is computed by multiplying the vector sum 254 by the scalar 1/N. The median minimal distance vector basically constitutes a measure of how the point cloud should be translated in X Y and Z directions in order to better fit to the digital object. Now, the registration process computes a rotation factor, which is explained by steps 5-8 of FIG. 11B, to indicate how the point cloud needs to be rotated in order to better fit the digital object. In an alternative arrangement, a rotation factor could be computed to indicate how the digital object would need to be rotated in order to better fit the point cloud.

In FIG. 11B, at step 5 (216), the X, Y and Z components of the median minimal distance vector is subtracted from every point in the point cloud. This is performed by making a copy of the point cloud coordinates and operating on the copy as an interim step in the procedure, the underlying data from the point cloud is unchanged. At the same step the "center of mass" of the points of the point cloud which are not excluded by step 2 is calculated. The "center of mass" is defined as the vector sum of position vectors of all mentions points scaled by the inverse of the number of points.

At step 6 (218) a calculation is made of the cross product of two vectors for every point in the point cloud. The two vectors are as follows: 1) a position vector Vi extending from the origin 253 of the global coordinate system to the points in the point cloud, subtracted by the vector of the center of mass of the remaining points of the point cloud as calculated in step 5, and 2) the identified minimum distance vector Ni for that point.

At step 7 (220), a calculation is made of the vector sum of the cross vectors calculated in step 6, that is the net cross vector $$\sum_j (v_j \times n_j)$$

for all i points in the frame i, where x is the cross product operator.

At step 8 (222), the vector sum of step 7 is weighted against the inverse of the sum of all squares of the position vectors (Vi) of the points in the point cloud, to arrive at a rotation vector U. U is interpreted as follows: The direction of U gives us the rotation axis and the magnitude of U is the angle or amount of rotation. In particular, if we consider Vi to be the position vectors from the origin of the coordinate system to the vertex of every point, and Ni being the minimal distance vectors defined above, then the weighting is as follows:

$$U = \frac{\sum_j (v_j \times n_j)}{\sum_j v_j^2}$$

The reasoning behind this weighting is as follows. If you imagine the distance vectors as the realization of linear spring elements, the vector sum of the cross products represents the aggregate moment, or rotational discrepancy, generated between the point cloud and the object. In the case of small deviations between the position of the point cloud and its final position, it can be assumed that the rotational moment also determined the direction of the necessary adjustment. The scaling with the help of the inverse of the sum of the squares of the position vectors considers the global extension of the point cloud. That is, the larger the distances of the points from the center, the larger is the ratio of rotational moment and angle between the present position and the target position. In a global sense, the mentioned factor (inverse of the sum of squares of position vectors) describes this ratio.

At step 9, the result of step 8 is scaled with an empirical "acceleration factor" f. The factor f serves to possibly accelerate this convergence. A value of f of greater than 1 is appropriate for relatively large rotational displacements, but in any event has to be determined empirically.

At step 10 (226), the result of step 9 is interpreted as an axis of rotation, the magnitude of which indicates the amount by which the point cloud has to be rotated in order to make the local overlapping areas of the point cloud and the object lie within each other. The magnitude of the rotation vector is interpreted as the angle around which the point cloud has to be rotated. In an alternative arrangement, a magnitude of rotation vector may derived so as to describe an angle around which the object is rotated.

A rotation transformation matrix [T] (R) is calculated for the point cloud. This formula shows how to convert the rotation vector resulting from step 9, where $\beta$ is the original length of the net cross vector which equals the angle of rotation that is required to fit the overlapping areas of frame i to the digital object and u is the unit vector of U,, $$u = \frac{U}{|U|}$$

with components $u_x, u_y, u_z$.

$$[T](R) = \begin{pmatrix} (1-\cos\beta)u_x^2 + \cos\beta & (1-\cos\beta)u_x u_y - u_z \sin\beta & (1-\cos\beta)u_x u_z + u_y \sin\beta \\ (1-\cos\beta)u_y u_x + u_z \sin\beta & (1-\cos\beta)u_y^2 + \cos\beta & (1-\cos\beta)u_y u_z - u_x \sin\beta \\ (1-\cos\beta)u_z u_x - u_y \sin\beta & (1-\cos\beta)u_z u_y + u_x \sin\beta & (1-\cos\beta)u_x^2 + \cos\beta \end{pmatrix}$$

To obtain a unique transformation operator for calculating the translation and the rotation transformation in a closed manner a 4×4 matrix representation is used. The relation between the 4×4 representation and the three dimensional rotation represented by 3×3 Matrix [T](R) is as follows $$[T_4](R) = \begin{pmatrix} [T](R) & 0 \\ 0 & 1 \end{pmatrix}$$

and between the 4×4 representation and the three dimensional translation, represented by vector (t)

$$[T_4](t) = \begin{pmatrix} 1 & 0 & 0 & t_x \\ 0 & 1 & 0 & t_y \\ 0 & 0 & 1 & t_z \\ 0 & 0 & 0 & 1 \end{pmatrix}$$

To apply this 4×4 matrix on the three dimensional vectors the following convention is made: A three dimensional vector is transformed into the 4 dimensional vector space by identifying the first three components of the 4 vector with the components of the three dimensional vector but the fourth component is always unique. $(x,y,z)^T \rightarrow (x,y,z,1)^T$ At step 11 (228 in FIG. 11C), a transformation matrix for the point cloud, [T₄](i), is calculated by multiplying the rotation matrix [T₄] (R) (from right) by the translation matrix [T₄](t) from step 4 [T₄](i)=[T₄](R)g[T₄](t).

The point cloud can be separately and independently operated on by the rotation matrix and the translation vector. Alternatively, the digital object can be separately and independently operated on by a rotation matrix and a translation vector.

At step 12 (230), a calculation is made of the square root of the sum of the squares of the minimum distance vectors calculated in step 1 (210) of FIG. 11A divided by the number of vectors, which denotes the closeness factor quality of the registration in this iteration, value MA below. At step 13 (232) the closeness factor MA is compared to the required closeness factor MA computed at step 1 (210). (e.g., this closeness factor for certain known digital images (such as dental appliances) may be 100 microns). If the value MA is larger than the required closeness factor to terminate the registration process, in which case the registration process returns to Step 2 (212) and is repeated another iteration.

If the closeness factor MA is less than the quality index, than registration process ends. For example, this may occur when the closeness factor MA does not improve by at least some amount per iteration (say 1 percent) after 10 iterations, the process is deemed complete.

FIG. 12 illustrates that a range variable R can be used to filter or limit the number of points that are used when calculating net normal vectors, triangle surface, cross vectors, etc. The purpose of the range variable R is to screen out stray data points far from the triangle surface of the point cloud. The stray data has the effect of skewing the entries of the transformation matrix and increasing the number of iterations until the quality index is met.

Figure 13:
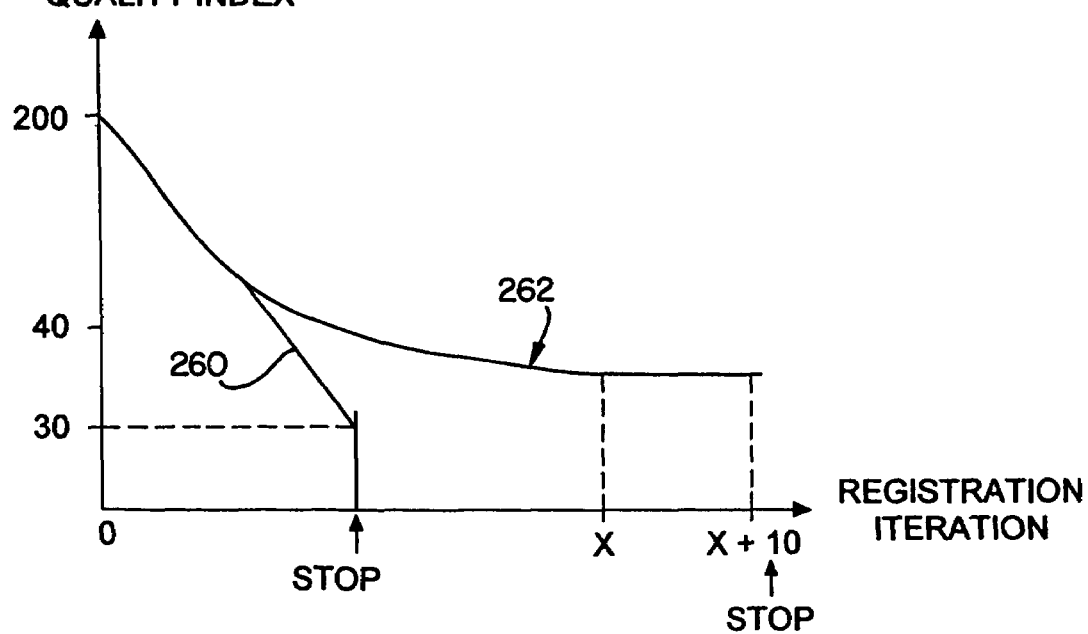
FIG. 13 is an illustration of the closeness factor or quality index, measured as the magnitude of the net normal vector $N_{net}$ showing how the quality index can improve with successive iterations of the registration process.

FIG. 13 illustrates two ways in which the point cloud to object registration process may terminate. As shown by line 260, the process may terminate when the closeness factor MA goes below the quality index threshold. For example, where the digital image is a bracket bonded to a tooth, this quality index may be set at 100 microns. Alternatively, the closeness factor MA may level off at some value above the quality index, despite further iterations of steps 1-13 of FIGS. 11A-C. This is indicated by line 262. When the closeness factor MA does not improve by at least some amount per iteration (say 1 percent) after 10 iterations, the process is deemed complete. Here, the designation x indicates the iteration in which the amount of improvement in the quality index from the previous iteration to that iteration was first less than a threshold, e.g., 1 percent.

Figure 14:
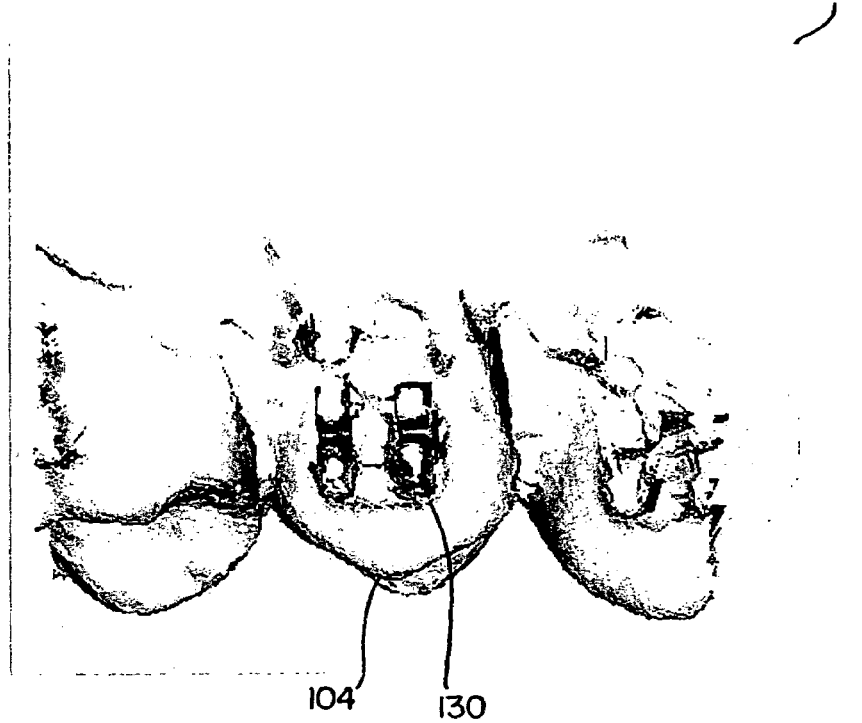
FIG. 14 is a screen-shot of the bracket model registered to the bracket scan data after bracket registration has been completed.
Figure 15:
FIG. 15 is a screen shot of a close up view the virtual tooth after the bracket registration process is completed.

Once the bracket registration algorithm has been completed, a registered bracket model can be displayed on a display. For example, FIG. 14 illustrates a screen shot comprising a subset of scan data 280. This sub-set of scan data 280 now includes the tooth scan data 104 illustrated in FIG. 8 with the digital bracket image registered to the bracket scan data 103 such that the bracket model is now positioned in 3-D space according to the previously described registration algorithm. The digital bracket model 130 is illustrated as registered on the tooth scan data 104. A comparison of FIG. 10 (bracket scan data prior to registration) and FIG. 14 (bracket scan data after registration) illustrates how the digital bracket model is rotated and translated in three-dimensional space to find a best fit to the bracket scan data.

The scan data 280 may now be used to revise the complete 3-D dentition model or rather update the patient's original scan containing the poor original bracket scan data. FIG. 19 illustrates a three dimensional model of the tooth with the registered bracket model in FIG. 18. The bracket registration process is performed for the other remaining brackets of the patient's dentition.

Oftentimes, certain errors may arise during the bracket registration process. For example, there may be actual differences between what in the registration process illustrates in FIG. 18 and how the actual bracket looks. For example, because of poor scanning techniques or discrepancies bracket model information, there may circumstances where the resulting scan data is so poor that the registration algorithm is unable to register the model. In these situations, the best-fit operating parameters of the processing may need to be modified, including the MA value.

In addition, there may also be situations wherein the operator initiating the registration process perceives a discrepancy between the registered bracket and the actual bracket. The operator may not agree with the resulting registration result or may wish to alter the result for a particular reason. For example, the operator may note that the registered bracket data (bracket location) is in conflict with the actual bracket location. Such a conflict may arise where the bracket has certain deformities (bent wing, scratch, broken, etc.). In one arrangement, the operator initiating the bracket registration process will be able to override the bracket registration results and reposition the digital bracket model in space. This model manipulation may take place using various model manipulation icons.

After bracket registration has been completed, there may be a further need to obtain a new or a revised virtual model of the tooth underlying the registered bracket in the model. For example, the orthodontist may wish to see if the tooth has undergone movement since the previous scan or since treatment has begun. Alternatively, a tooth model may be required since an original tooth model does not already exist. This may occur, for example, where the patient undergoing the treatment is a new patient of the treating orthodontist and already has brackets installed on the teeth, or for one reason or another, the patient had not already undergone an original scan without any alliance placed on the teeth.

In such a situation, after bracket registering and, if required, operator override, the process will begin by modeling the tooth underlying the bonded bracket. That is, the previously. described frame to object registration algorithm will now determine where the tooth resides in three dimensional space.

Figure 16:
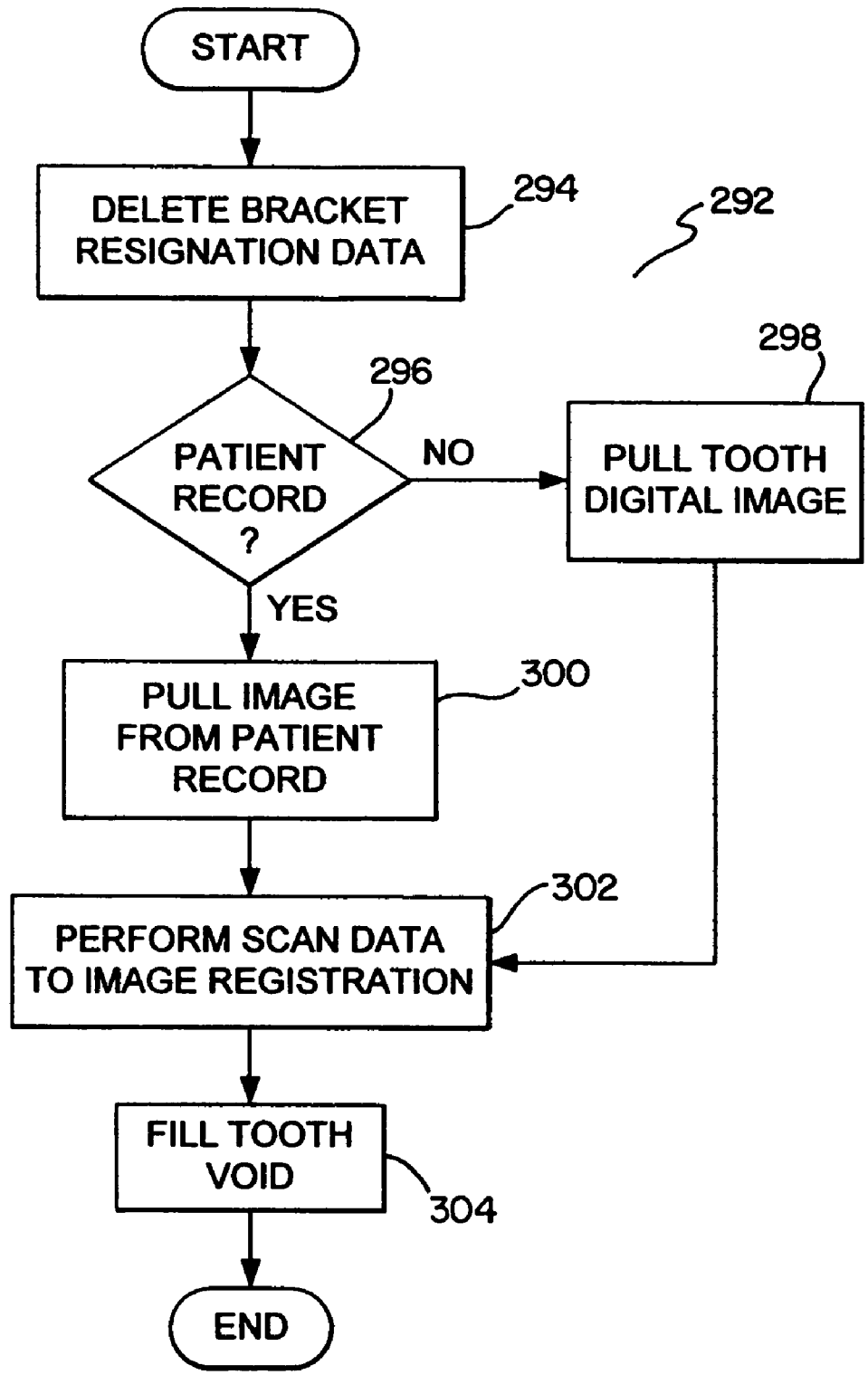
FIG. 16 provides a process for finding a best fit between a virtual tooth model and the tooth scan data illustrated in FIG. 15.
Figure 17:
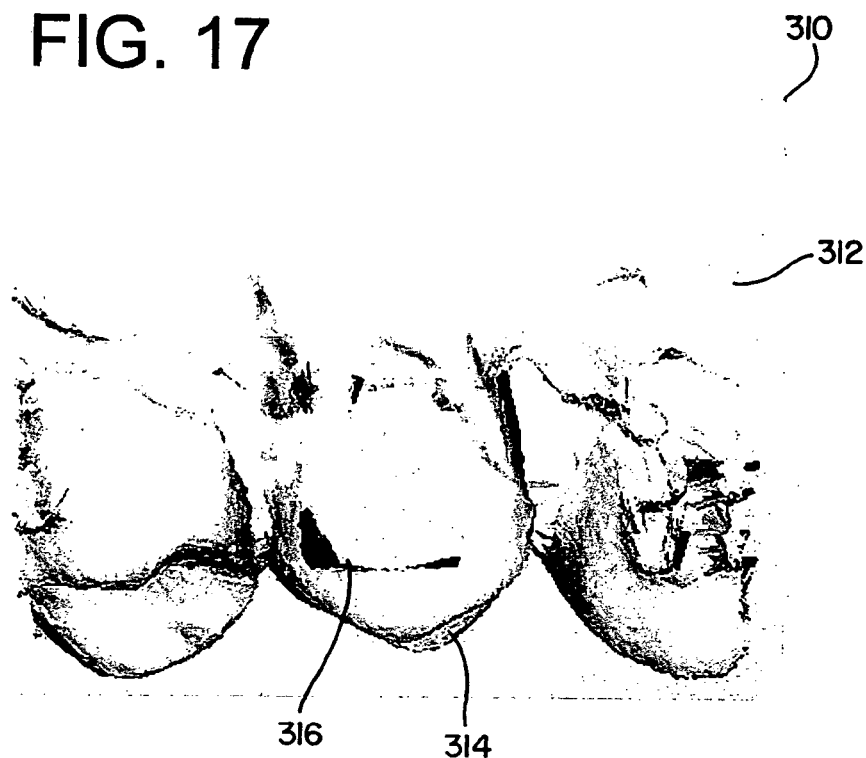
FIG. 17 is a screen shot of the virtual image of FIG. 14 with the bracket scan data omitted.

FIG. 16 provides a flowchart 292 for tooth registration after bracket registration has been completed. As a first step 294, the tooth registration process will delete the scan data that is in close vicinity to the registered bracket model (e.g., 0.3 mm). Deleting this registered bracket data will provide a virtual tooth model having a data void. For example, FIG. 17 illustrates a screen shot 310 comprising a scan data set 312. Scan data set 312 includes scan data for various teeth, including the subject tooth 314. Comparing the screen shot 310 of FIG. 17 and the screen shot 280 of FIG. 14, one can see that the registered bracket image 130 of FIG. 14 has been omitted thereby creating a scan data void 316.

Next, at step 296, the process determines whether a patient data record exists. Where the patient is a new patient, the operator will have to initiate creating a patient data record. In this scenario, no preexisting virtual model of the tooth 314 exists. Therefore, a digital object having a predefined geometry such as a template virtual tooth is pulled from a digital library at step 298, preferably stored either at the back office server workstation 28 or the central server 32 (FIG. 1B). Once this digital object is pulled, the process begins by registering the tooth scan data to the digital object at step 302, similar to the process described in detail in FIGS. 11A-C.

If the process determines that a patient data record already exists at step 296, the virtual model for the tooth is pulled from the data record at step 300. Once the known digital tooth model is pulled from the patient record, the process begins to register the tooth scan data to the digital model at step 302. Once the tooth registration process has been completed, the scan data void 316 at step 304 is filled the 3-D surface data resulting from the registration process.

Figure 18:
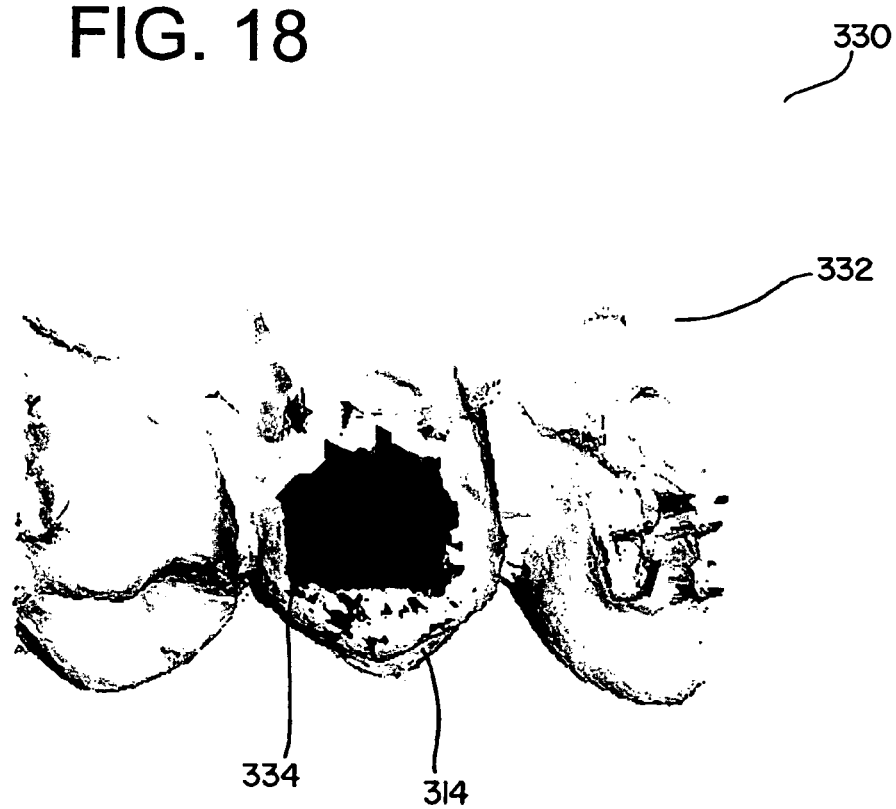
FIG. 18 is a screen shot of the virtual image of FIG. 13 with the tooth void registered to the tooth scan data after tooth model registration.
Figure 19:
FIG. 19 is a screen-shot of a virtual tooth after bracket and tooth registration.

FIG. 18 illustrates a modified screen shot 18 of what is illustrated in FIG. 17. In FIG. 18, the scan data 332 includes the tooth model 314 having the tooth void 316 (FIG. 17) filled with registered tooth surface 334. Now that both bracket and tooth registration has been completed, a new 3-D tooth model may be constructed. The patient data record may now be updated with this new information. FIG. 19 illustrates a virtual 3-D tooth having both a bracket surface and tooth surface resulting from the registration process.

SUMMARY

In summary, applicants have invented a novel method of constructing a virtual three-dimensional model (e.g. 3-D computer model 18) of an object. The method comprises the steps of:

scanning the object (e.g., a patient's dentition);

creating a three-dimensional virtual model (18) of the object from the scanning step with the aid of a computer (e.g., back office system 28, or central server 32). The three-dimensional virtual model has a first portion (e.g., bracket data 103) thereof corresponding to scanning of a known structure (e.g., a bracket model 130) forming a part of the object. The known structure of predetermined three-dimensional configuration and wherein the first portion (103) is a less than an ideal three-dimensional representation of the known structure (e.g., a bracket model 130);

retrieving a three-dimension virtual object (130) from a memory (28,32), the three-dimensional virtual object corresponding to the known structure;

registering (e.g., using software as described herein) the three-dimensional virtual object to the first portion (103) of the three-dimensional virtual model to form a three-dimensional surface; and forming the virtual three-dimensional model of the object, the three-dimensional model including the three-dimensional surface.

Applicants have also invented a novel workstation adapted to form three-dimensional virtual models (18) of objects. The workstation includes a central processing unit (28,32) and a memory storing a three-dimensional virtual model (18) of an object. The three-dimensional virtual model has a first portion (103) thereof corresponding to scanning of a known structure forming a part of the object. The memory further stores a three-dimensional virtual object (130) corresponding to the known structure. Software is executable by the central processing unit for registering the three-dimensional virtual object to the first portion to form a three-dimensional surface and for forming a virtual three-dimensional model of the object. (340) The virtual three-dimensional model of the object including the three-dimensional surface.

Applicants have also invented a novel apparatus for constructing a virtual three-dimensional model of an object. The apparatus comprises:

means for scanning (e.g., such as a hand held or laser scanner) the object;

means for creating a three-dimensional virtual model (e.g., a computer loaded with software) of the object from the scanning step, the three-dimensional virtual model having a first portion thereof corresponding to scanning of a known structure forming a part of the object, the known structure of predetermined three-dimensional configuration (e.g., having a digital model of the part of the object), wherein the first portion is a less than an ideal three-dimensional representation of said known structure;

means for retrieving (e.g., software as described herein) a three-dimension virtual object from a memory, said three-dimensional virtual object corresponding to said known structure;

means for registering (e.g., software executing algorithm described herein) the three-dimensional virtual object to the first portion of the three-dimensional virtual model to form a three-dimensional surface; and means for forming (e.g., software as described herein) the virtual three-dimensional model of the object, the three-dimensional model including said three-dimensional surface.

Applicants have also invented a novel method of constructing a virtual three-dimensional model of an object having a predefined geometry from a scanner (e.g., a hand held scanner or a laser scanner), a data processing system (e.g., back office 22, or central server 26)), and at least one machine-readable memory accessible to the data processing system. The method includes the steps of:

(a) scanning the object with the scanner in order to receive a data set related to said object;

(c) obtaining a stored digital image of said object having a known geometry; and (d) processing said data set resulting from said scan so as to register said scan data relative to said stored digital image.

Applicants have also invented a method of constructing a virtual three-dimensional model of an object having a predefined geometry from a scanner, a data processing system, and at least one machine-readable memory accessible to the data processing system. The method includes the steps of:

(a) scanning the object with the scanner and thereby obtaining a first and a second two-dimensional image of the object, wherein during scanning the scanner and object are moved relative to each other;

(d) processing the first and second image with the data processing system so as to convert the two-dimensional images into a data set representing a point cloud comprising individual points, each point expressed as a location in a three-dimensional coordinate system;

(e) obtaining a stored digital image of the object having a predefined geometry; and (d) further processing the data representing the point cloud with the data processing system so as to register the point cloud relative to the stored digital image to thereby produce a three-dimensional virtual model of the object substantially consistent with the frame.

Applicants have also invented a novel method of determining a location of a virtual three-dimensional model of an object of known geometry. The novel method includes the steps of:

a) scanning said known object in a series of scans, each scan generating a set of images;

d) converting said set of images into a point cloud;

e) retrieving a digital representation of said virtual three-dimensional known object from memory; and d) registering said point cloud to said digital representation to thereby verify in three-dimensional space a position of said virtual three-dimensional model.

It is contemplated that the inventive registration system and method of registration can be used on virtually any type of digital object of known geometry. The basic idea is that a virtual object is retrieved from memory and a registration is performed of the stored virtual object to the scan data, and then replace the scan data with the resulting 3-D surface from the registration. The medical field is only one example of where three-dimensional information of a surface may be a valuable piece of information, and can be easily and quickly attained with the scanning system of the present invention. These other possible uses of the scanner for other types of objects are considered within the scope of the invention.

In one disclosed arrangement, if a component (e.g., a portion of a bracket) of an object (e.g., a 3-D model of a tooth and a bracket) having a predetermined three-dimensional configuration is to be located with respect to the object, a registration process will be the first step used to receive the best fit of a digital representation of the component, retrieved from a computer memory, and the surface data acquired of the object and its component. Having received the best fit, the next step is to utilize this result. Depending on the task to be fulfilled, there are several options.

In one example, it is possible to simply "merge" the surfaces of the digital representation with the surfaces acquired by the scanning process. Doing this, missing parts or intentional voids in the scan data could be completed in order to provide a more complete representation of the object and its components than could be provided by the scan. The result would be an improved or a complete representation of a surface of the object.

Another option would be to export the transformation matrix as a result of the registration process. For example, other algorithms could import these data sets for further processing. For instance, if a printed circuitry board has been scanned, it would be possible to retrieve the known digital representations of the components used on this board (e.g., transistors, capacitors, integrated circuits etc.) and perform a registration for each component and sub-element in order to receive a best fit of the digital representations to the scan data. In one arrangement, the transformation matrices could be exported to PC board layout software, thus enabling this software to arrange the components according to the scanned PC board.

In an orthodontic application, these transformation matrices could be useful in order to design a wire that is supposed to run through the various slots of bonded orthodontic brackets. If the brackets are being scanned, and their location with respect to each other or with respect to the teeth is determined by the registration process, the transformation matrices could be fed into an algorithm that has knowledge of the location of the bracket slot with respect to the local coordinate system of the bracket. Therefore, such an algorithm could define the shape of the wire by first calculating the location of the local bracket coordinate system by using the transformation matrix. And then in a second step, calculate the location of the slot basing on the location of the local coordinate system.

A further option would be to export the complete component after the best fit has been received. Doing this, the transformation matrix resulting from registration would be applied to the component, thus referencing each data point of the component not to its local coordinate system any more, but to the global coordinate system.

Another option would be to perform this step only to portions of the component that are of particular interest. Such a portion could be the data defining the slot of a bracket. As used herein, locating an object is therefore a general term that is meant to refer to providing data resulting from receiving the best fit.

Variations from the illustrated techniques is contemplated without departure from the scope of the invention. This true scope is to be ascertained by reference to the appended claims.

The invention claimed is:

1. A method of constructing a virtual three-dimensional model of an object, wherein said object comprises a first object attached to a second object, comprising the steps of:
    scanning said object;
    creating a scanned virtual three-dimensional model of said object from a point cloud obtained from said scanning step with the aid of a computer, said scanned virtual three-dimensional model having a first portion thereof corresponding to scanning of said first object, wherein said first object is of a known structure, said known structure of predetermined three-dimensional configuration, wherein said first portion is a less than an ideal three-dimensional representation of said known structure;
    retrieving a pre-existing three-dimensional digital model from a memory, said three-dimensional digital model corresponding to said known structure;
    registering said pre-existing three-dimensional digital model to a portion of said point cloud corresponding to said first portion to form a three-dimensional surface;
    wherein said registering step comprises calculating minimum distance vectors from every point in said portion of said point cloud to said pre-existing three-dimensional digital model and excluding those points from said three dimensional surface whose minimum distance vectors exceed a predefined value; and
    forming said virtual three-dimensional model of said object from said scanned virtual three-dimensional model of said object, said virtual three-dimensional model including said three-dimensional surface.

2. The method of claim 1, wherein said pre-existing three-dimensional digital model comprises a pre-existing three-dimensional digital model of an orthodontic appliance.

3. The method of claim 2, further comprising the steps of storing a library of pre-existing three-dimensional digital models of orthodontic appliances and selecting one of said pre-existing three-dimensional digital models of orthodontic appliances for said step of registration.

4. The method of claim 1, wherein said step of scanning is performed with a hand-held scanner using a projection pattern and an image pick-up to acquire three-dimensional information as to said object.

5. The method of claim 1, wherein said second object comprises an anatomical structure.

6. The method of claim 5, wherein said anatomical structure comprises teeth and wherein said known structure comprises an orthodontic appliance.

7. The method of claim 6, wherein said orthodontic appliance comprises an orthodontic bracket.

8. The method of claim 1, further comprising the steps of deleting said first portion and replacing said first portion with said three-dimensional surface resulting from said registration step.

9. The method of claim 1, further comprising the step of deleting said first portion and forming a second virtual three-dimensional model of said object by replacing said first portion with a second three-dimensional surface representing said object without said known structure.

10. The method of claim 1, wherein said object comprises at least one tooth and a bracket, and wherein said known structure comprises said bracket.

11. A workstation adapted to form a virtual three-dimensional model of an object, wherein said object comprises a first object attached to a second object, comprising:

a central processing unit;

a memory storing a scanned virtual three-dimensional model of said object in the form of a point cloud obtained from scanning said object, said scanned virtual three-dimensional model having a first portion thereof corresponding to scanning of said first object, wherein said first object is of a known structure; said known structure of predetermined three-dimensional configuration, wherein said first portion is a less than an ideal three-dimensional representation of said known structure;

said memory further storing a pre-existing three-dimensional digital model corresponding to said known structure; and software executable by said central processing unit for registering said pre-existing three-dimensional digital model to a portion of said point cloud corresponding to said first portion to form a three-dimensional surface; wherein said software for registering comprises software for calculating minimum distance vectors from every point in said portion of said point cloud to said pre-existing three-dimensional digital model and excluding those points from said three dimensional surface whose minimum distance vectors exceed a predefined value; and for forming the virtual three-dimensional model of said object from said scanned virtual three-dimensional model of said object, said virtual three-dimensional model of said object including said three-dimensional surface.

12. The workstation of claim 11, wherein said pre-existing three-dimensional digital model comprises a pre-existing three-dimensional digital model of an orthodontic appliance.

13. The workstation of claim 12 wherein said memory further comprises a library of pre-existing three-dimensional digital models of orthodontic appliances and selecting one of said pre-existing three-dimensional digital models of orthodontic appliances for registering said pre-existing three-dimensional digital model to said first portion.

14. The workstation of claim 11, further comprising a hand-held scanner using a projection pattern and an image pick-up to acquire three-dimensional information as to said object.

15. The workstation of claim 11, wherein said second object comprises an anatomical structure.

16. The workstation of claim 15, wherein said anatomical structure comprises teeth and wherein said known structure comprises an orthodontic appliance.

17. The workstation of claim 16 wherein said orthodontic appliance comprises a tooth bracket.

18. The workstation of claim 11, wherein said software executable by said central processing unit includes instructions for deleting said first portion and and instructions for replacing said first portion with said three-dimensional surface resulting from said registration step.

19. The workstation of claim 11, wherein said software executable by said central processing unit includes instructions for deleting said first portion, and instructions for replacing said first portion with a second three-dimensional surface representing said object without said known structure, thereby forming a second three-dimensional virtual model of said object.

20. The workstation of claim 11, wherein said object comprises at least one tooth and a bracket, and wherein said known structure comprises said bracket.

21. An apparatus for constructing a virtual three-dimensional model of an object, wherein said object comprises a first object attached to a second object, comprising:

means for scanning said object;

means for creating a scanned virtual three-dimensional model of said object in the form of a point cloud from said scanning step with the aid of a computer, said scanned virtual three-dimensional model having a first portion thereof corresponding to scanning of said first object, wherein said first object is of a known structure, said known structure of predetermined three-dimensional configuration, wherein said first portion is a less than an ideal three-dimensional representation of said known structure;

means for retrieving a pre-existing three-dimensional digital model from a memory, said pre-existing three-dimensional digital model corresponding to said known structure;

means for registering said pre-existing three-dimensional digital model to a portion of said point cloud corresponding to said first portion to form a three-dimensional surface; wherein said means for registering comprise means for calculating minimum distance vectors from every point in said portion of said point cloud to said pre-existing three-dimensional digital model and excluding those points from said three dimensional surface whose minimum distance vectors exceed a predefined value; and means for forming said virtual three-dimensional model of said object from said scanned virtual three-dimensional model of said object, said virtual three-dimensional model including said three-dimensional surface.

22. The apparatus of claim 21, wherein said pre-existing three-dimensional digital model comprises a pre-existing three-dimensional digital model of an orthodontic appliance.

23. The apparatus of claim 21, further comprising a library of stored pre-existing three-dimensional digital models of orthodontic appliances, wherein one of said pre-existing three-dimensional digital models of orthodontic appliances is selected for registering said pre-existing three-dimensional digital model to said first portion to form a three-dimensional surface.

24. The apparatus of claim 21, further comprising a hand-held scanner using a projection pattern and an image pick-up to acquire three-dimensional information as to said object.

25. The apparatus of claim 21, wherein said second object comprises an anatomical structure.

26. The apparatus of claim 21, wherein said anatomical structure comprises teeth and wherein said known structure comprises an orthodontic appliance.

27. The apparatus of claim 26, wherein said orthodontic appliance comprises an orthodontic bracket.

28. The apparatus of claim 21, further comprising means for deleting said first portion and means for replacing said first portion with said three-dimensional surface resulting from said registration step.

29. The apparatus of claim 21, further comprising means for deleting said first portion, means for replacing said first portion with a second three-dimensional surface representing said object without said known structure, thereby forming a second three-dimensional virtual model of said object.

30. The apparatus of claim 21, wherein said object comprises at least one tooth and a bracket, and wherein said known structure comprises said bracket.

31. A method of constructing a virtual three-dimensional model of an object having a predefined geometry from a scanner, a data processing system, and at least one machine-readable memory accessible to the data processing system, comprising the steps of:

(a) scanning the object with the scanner and responsively obtaining a three-dimensional surface of said object in the from a point cloud; wherein said three-dimensional surface of said object is a less than an ideal three-dimensional representation of said object;

(b) obtaining a pre-existing three-dimensional digital model of said object from said memory; and (c) registering said three-dimensional surface in the from said point cloud to said pre-existing three-dimensional digital model to thereby produce the virtual three-dimensional model of said object; wherein said registering step comprises calculating minimum distance vectors from every point in said point cloud to said pre-existing three-dimensional digital model and excluding those points from said three dimensional surface whose minimum distance vectors exceed a predefined value.

32. A method of constructing a virtual three-dimensional model of an object having a predefined geometry from a scanner, a data processing system, and at least one machine-readable memory accessible to the data processing system, comprising the steps of:

(a) scanning the object with the scanner and thereby obtaining a first and a second two-dimensional images of the object, wherein during scanning the scanner and object are moved relative to each other;

(b) processing the first and second images with the data processing system so as to convert the two-dimensional images into a data set representing a point cloud comprising individual points, each point comprising a location in a three-dimensional coordinate system;

(c) obtaining a pre-existing three-dimensional digital model of the object; and (d) further processing the data set representing the point cloud with the data processing system so as to register the point cloud relative to the pre-existing three-dimensional digital model to thereby produce the virtual three-dimensional model of the object; wherein said registering step comprises calculating minimum distance vectors from every point in said point cloud to said pre-existing three-dimensional digital model and excluding those points from said virtual three-dimensional model of the object whose minimum distance vectors exceed a predefined value.

33. The method of claim 32, wherein a spatial transformation relationship is derived for the point cloud and stored in the memory, the spatial transformation relationship indicating how the points in the point cloud should be translated and rotated in a three-dimensional coordinate system to register the point cloud relative to the pre-existing three-dimensional digital model.

34. The method of claim 32, wherein in step (d) an operator manipulates the virtual three-dimensional model of said object.

35. The method of claim 32, wherein step (d) is initiated by placing a virtual marker on a representation of the object.

36. The method of claim 32 wherein said object comprises an orthodontic appliance, and wherein said two-dimensional images of said object are obtained during a monitoring scan initiated after the orthodontic treatment using the orthodontic appliance has commenced.

37. The method of claim 32 wherein the pre-existing three-dimensional digital model is retrieved from a digital library comprising a plurality of pre-existing three-dimensional digital models.

38. The method of claim 32, wherein the scanner comprises a hand-held scanning device and the object is scanned by moving said hand-held scanning device over said object.

39. The method of claim 32, wherein the object comprises a dental appliance.

40. The method of claim 39, wherein the dental appliance comprises a bracket.

41. The method of claim 32, wherein the data processing system is incorporated into a workstation for said scanner.

42. A method of determining a location of a virtual three-dimensional model of an object of known geometry, comprising the steps of:

a) scanning said known object and generating a set of images;

b) converting said set of images into a point cloud;

c) retrieving said virtual three-dimensional model of said object from memory; and d) registering said point cloud to said virtual three-dimensional model of said object to thereby verify in three-dimensional space the position of said virtual three-dimensional model of said object; wherein said registering step comprises calculating minimum distance vectors from every point in said point cloud to said virtual three-dimensional model of said object and excluding those points from said virtual three-dimensional model of said object whose minimum distance vectors exceed a predefined value.

43. A method of registering a first digital model of a dental appliance to a three-dimensional representation of said dental appliance as a result of scanning, comprising the steps of: p1 a) scanning said dental appliance and generating a first set of images;

b) converting said first set of images into a three-dimensional representation of said dental appliance in the form of a point cloud;

c) retrieving said first digital model of said dental appliance from a digital library;

d) fitting said three-dimensional representation in the form of said point cloud to said first digital model to thereby register said first digital model to said three-dimensional representation and generate a revised three dimensional representation of the dental appliance; wherein said registering step comprises calculating minimum distance vectors from every point in said point cloud to said first digital model of said object and excluding those points from said three-dimensional representation whose minimum distance vectors exceed a predefined value.

44. The method of claim 43 further comprising the steps of scanning a second known object and generating a second set of images;

converting said second set of images into a second point cloud;

deleting said registered first digital model from said revised three dimensional representation;

retrieving a second digital model of said second known object from a digital library;

performing a best fit analysis of said second point cloud to said second digital model to thereby register said second digital model to said second point cloud and generate a second revised three dimensional representation.

45. The method of claim 44 wherein said second digital model is a virtual digital tooth model.

* * * * *